United States Patent
Einav et al.

(10) Patent No.: US 11,887,714 B2
(45) Date of Patent: *Jan. 30, 2024

(54) APPARATUSES AND METHODS FOR HANDLING PILLS WITHIN PHARMACEUTICAL DISPENSING DEVICES

(71) Applicant: Tech Pharmacy Services, LLC, Fort Lee, NJ (US)

(72) Inventors: Omer Einav, Kfar-Monash (IL); Doron Shabanov, Tzur-Yigal (IL); Tamir Ben David, Tel-Aviv (IL); Eyal Livschitz, Givat Shmuel (IL); Thomas A. McKinney, Boonton, NJ (US); Moshe Liberman, Yehud (IL)

(73) Assignee: Tech Pharmacy Services, LLC, Fort Lee, NJ (US)

( * ) Notice: Subject to any disclaimer, the term of this patent is extended or adjusted under 35 U.S.C. 154(b) by 22 days.

This patent is subject to a terminal disclaimer.

(21) Appl. No.: 17/544,968

(22) Filed: Dec. 8, 2021

(65) Prior Publication Data
US 2022/0101976 A1 Mar. 31, 2022

Related U.S. Application Data

(63) Continuation of application No. 16/737,943, filed on Jan. 9, 2020, now Pat. No. 11,238,970, which is a continuation-in-part of application No. 16/430,456, filed on Jun. 4, 2019, now Pat. No. 10,964,154.

(51) Int. Cl.
*G16H 20/13* (2018.01)
*G16H 40/60* (2018.01)

(52) U.S. Cl.
CPC ............. *G16H 20/13* (2018.01); *G16H 40/60* (2018.01)

(58) Field of Classification Search
CPC ..................................................... G16H 20/13
See application file for complete search history.

(56) References Cited

U.S. PATENT DOCUMENTS

| 5,405,048 | A | 4/1995 | Rogers et al. |
| RE35,743 | E | 3/1998 | Pearson |
| (Continued) | | | |

FOREIGN PATENT DOCUMENTS

| EP | 2457550 | 4/2016 |
| WO | WO 01/21131 | 3/2001 |
| (Continued) | | |

OTHER PUBLICATIONS

Supplementary European Search Report and the European Search Opinion dated Aug. 1, 2022 From the European Patent Office Re. Application No. 19896179.9. (8 Pages).

(Continued)

*Primary Examiner* — Gene O Crawford
*Assistant Examiner* — Ayodeji T Ojofeitimi

(57) ABSTRACT

A method of dispensing medication from a plurality of medication containers, using a dispensing system for collecting a medication dosage from a medication container including: receiving a medication selection; selecting a medication container, from the plurality of medication containers, based on the medication selection; matching a collection protocol to be applied to the medication container including one or more parameter for control of the dispensing system; and dispensing the medication selection from the medication container according to the collection protocol.

36 Claims, 15 Drawing Sheets

(56) References Cited

U.S. PATENT DOCUMENTS

| | | | |
|---|---|---|---|
| 6,006,946 | A | 12/1999 | Williams et al. |
| 6,529,801 | B1 | 3/2003 | Rosenblum |
| 7,698,019 | B2 | 4/2010 | Moncrief et al. |
| 8,027,849 | B2 | 9/2011 | Johnson et al. |
| 8,219,243 | B2 | 7/2012 | Haas |
| 8,280,550 | B2 | 10/2012 | Levy et al. |
| 8,521,327 | B2 | 8/2013 | Pinney et al. |
| 8,991,138 | B2 | 3/2015 | Yuyama et al. |
| 9,031,690 | B2 | 5/2015 | Cotner |
| 9,779,215 | B2 | 10/2017 | Rosenblum |
| 9,908,704 | B2 | 3/2018 | Hawkes et al. |
| 10,007,764 | B2 | 7/2018 | Kim |
| 10,049,188 | B2 | 8/2018 | Iantorno et al. |
| 10,614,916 | B1 | 4/2020 | Einav et al. |
| 10,959,917 | B2 | 3/2021 | Einav et al. |
| 10,964,154 | B2 | 3/2021 | Einav et al. |
| 11,238,970 | B2 * | 2/2022 | Einav ............... G16H 40/60 |
| 2003/0024943 | A1 | 2/2003 | MacDonald |
| 2004/0155049 | A1 | 8/2004 | Float et al. |
| 2005/0049746 | A1 | 3/2005 | Rosenblum |
| 2005/0259818 | A1 | 11/2005 | Silverbrook et al. |
| 2009/0321469 | A1 | 12/2009 | Knoth |
| 2010/0300041 | A1 | 12/2010 | Kim |
| 2011/0017764 | A1 | 1/2011 | Liguori et al. |
| 2011/0251850 | A1 | 10/2011 | Stephens |
| 2011/0315588 | A1 | 12/2011 | Ross et al. |
| 2012/0004770 | A1 | 1/2012 | Ooyen et al. |
| 2012/0187141 | A1 | 7/2012 | Young et al. |
| 2012/0209619 | A1 | 8/2012 | Knotts et al. |
| 2012/0259458 | A1 | 10/2012 | Barrett et al. |
| 2013/0092700 | A1 | 4/2013 | Braunstein |
| 2013/0123977 | A1 | 5/2013 | Sanders et al. |
| 2013/0240555 | A1 | 9/2013 | Kim |
| 2014/0058555 | A1 | 2/2014 | Rhoads, Jr. et al. |
| 2014/0262690 | A1 | 9/2014 | Henderson et al. |
| 2015/0081326 | A1 | 3/2015 | Krishnapuram et al. |
| 2015/0154709 | A1 | 6/2015 | Cook |
| 2016/0068328 | A1 | 3/2016 | 'T Lam et al. |
| 2016/0132404 | A1 | 5/2016 | Munson et al. |
| 2017/0132867 | A1 | 5/2017 | Berg et al. |
| 2017/0220768 | A1 | 8/2017 | Tanner, Jr. et al. |
| 2017/0267453 | A1 | 9/2017 | Hellenbrand |
| 2017/0312182 | A1 | 11/2017 | Ma |
| 2018/0122177 | A1 | 5/2018 | Este et al. |
| 2018/0357596 | A1 | 12/2018 | Bedford |
| 2020/0185076 | A1 | 6/2020 | Einav et al. |
| 2020/0323737 | A1 | 10/2020 | Einav et al. |
| 2020/0327980 | A1 | 10/2020 | Einav et al. |
| 2020/0388100 | A1 | 12/2020 | Einav et al. |
| 2020/0388369 | A1 | 12/2020 | Einav et al. |
| 2021/0201618 | A1 | 7/2021 | Einav et al. |
| 2021/0205178 | A1 | 7/2021 | Einav et al. |
| 2021/0225479 | A1 | 7/2021 | Einav et al. |
| 2021/0366599 | A1 | 11/2021 | Einav et al. |

FOREIGN PATENT DOCUMENTS

| | | |
|---|---|---|
| WO | WO 2004/036481 | 4/2004 |
| WO | WO 2005/043440 | 5/2005 |
| WO | WO 2018/052160 | 3/2018 |
| WO | WO 2020/121165 | 6/2020 |
| WO | WO 2020/208439 | 10/2020 |
| WO | WO 2020/208477 | 10/2020 |
| WO | WO 2020/208479 | 10/2020 |
| WO | WO 2020/245739 | 12/2020 |

OTHER PUBLICATIONS

Official Action dated May 18, 2022 From the US Patent and Trademark Office Re. U.S. Appl. No. 17/201,255. (33 Pages).
International Preliminary Report on Patentability dated Dec. 16, 2021 From the International Bureau of WIPO Re. Application No. PCT/IB2020/055232. (8 Pages).
International Preliminary Report on Patentability dated Oct. 21, 2021 From the International Bureau of WIPO Re. Application No. PCT/IB2020/053082. (6 Pages).
Notice of Allowance dated Oct. 27, 2022 From the US Patent and Trademark Office Re. U.S. Appl. No. 17/201,255. (9 Pages).
Applicant-Initiated Interview Summary dated Jul. 12, 2019 From the US Patent and Trademark Office Re. U.S. Appl. No. 16/379,831. (3 pages).
Final Official Action dated May 14, 2020 from the US Patent and Trademark Office Re. U.S. Appl. No. 16/214,081. (32 pages).
Final Official Action dated Aug. 23, 2021 from the US Patent and Trademark Office Re. U.S. Appl. No. 16/737,943. (10 pages).
International Preliminary Report on Patentability dated Jun. 24, 2021 From the International Bureau of WIPO Re. Application No. PCT/IB2019/060572. (8 Pages).
International Search Report and the Written Opinion dated Mar. 22, 2020 From the International Searching Authority Re. Application No. PCT/IB2019/060572. (14 Pages).
International Search Report and the Written Opinion dated Jun. 25, 2020 From the International Searching Authority Re. Application No. PCT/IB2020/052052. (10 Pages).
International Search Report and the Written Opinion dated Jun. 25, 2020 From the International Searching Authority Re. Application No. PCT/IB2020/053080. (13 Pages).
International Search Report and the Written Opinion dated Jun. 28, 2020 From the International Searching Authority Re. Application No. PCT/IB2020/053082. (13 Pages).
International Search Report and the Written Opinion dated Aug. 31, 2020 From the International Searching Authority Re. Application No. PCT/IB2020/055232.
Interview Summary dated Jul. 21, 2020 from the US Patent and Trademark Office Re. U.S. Appl. No. 16/430,456. (3 pages).
Interview Summary dated Jan. 8, 2021 from the US Patent and Trademark Office Re. U.S. Appl. No. 16/379,835. (4 pages).
Notice of Allowance dated Dec. 1, 2020 from the US Patent and Trademark Office Re. U.S. Appl. No. 16/430,456. (22 pages).
Notice of Allowance dated Dec. 10, 2020 From the US Patent and Trademark Office Re. U.S. Appl. No. 16/379,831. (18 Pages).
Notice of Allowance dated May 14, 2021 From the US Patent and Trademark Office Re. U.S. Appl. No. 16/379,835. (14 Pages).
Notice Of Allowance dated Nov. 19, 2019 From the US Patent and Trademark Office Re. U.S. Appl. No. 16/379,831. (3 pages).
Notice of Allowance dated Nov. 19, 2020 from the US Patent and Trademark Office Re. U.S. Appl. No. 16/559,716. (20 pages).
Notice of Allowance dated Sep. 29, 2021 from the US Patent and Trademark Office Re. U.S. Appl. No. 16/737,943. (5 pages).
Official Action dated Aug. 5, 2019 From the US Patent and Trademark Office Re. U.S. Appl. No. 16/379,831. (25 pages).
Official Action dated Sep. 9, 2019 From the US Patent and Trademark Office Re. U.S. Appl. No. 16/214,081. (33 pages).
Official Action dated May 15, 2019 From the US Patent and Trademark Office Re. U.S. Appl. No. 16/379,831. (24 pages).
Official Action dated Jul. 17, 2020 from the US Patent and Trademark Office Re. U.S. Appl. No. 16/559,716. (17 pages).
Official Action dated Jun. 24, 2021 from the US Patent and Trademark Office Re. U.S. Appl. No. 16/737,943. (34 pages).
Official Action dated Jun. 25, 2020 from the US Patent and Trademark Office Re. U.S. Appl. No. 16/430,456. (15 pages).
Official Action dated Nov. 25, 2020 From the US Patent and Trademark Office Re. U.S. Appl. No. 16/379,835. (38 Pages).
Restriction Official Action dated Apr. 2, 2019 From the US Patent and Trademark Office Re. U.S. Appl. No. 16/214,081. (6 pages).
Restriction Official Action dated Jul. 24, 2020 From the US Patent and Trademark Office Re. U.S. Appl. No. 16/379,835. (6 Pages).
Official Action dated Jun. 27, 2022 from US Patent and Trademark Office Re. U.S. Appl. No. 17/207,796. (38 pages).
International Preliminary Report on Patentability dated Oct. 21, 2021 From the International Bureau of WIPO Re. Application No. PCT/IB2020/052052. (7 Pages).

(56) References Cited

OTHER PUBLICATIONS

International Preliminary Report on Patentability dated Oct. 21, 2021 From the International Bureau of WIPO Re. Application No. PCT/IB2020/053080. (7 Pages).

* cited by examiner

```
┌─────────────────────────────────────────────────────────────────────┐
│ Receive medication request, for example, including medication type  │
│ and number of pills                                                 │
│ 400                                                                 │
└─────────────────────────────────────────────────────────────────────┘
                                    ↓
┌─────────────────────────────────────────────────────────────────────┐
│ Select medication container based on medication request and         │
│ optionally, medication container data                               │
│ 402                                                                 │
└─────────────────────────────────────────────────────────────────────┘
                                    ↓
┌─────────────────────────────────────────────────────────────────────┐
│ Optionally, receive pill property data and/or medication container  │
│ data                                                                │
│ 403                                                                 │
└─────────────────────────────────────────────────────────────────────┘
                                    ↓
┌─────────────────────────────────────────────────────────────────────┐
│ Optionally, select probe based on pill property data                │
│ 404                                                                 │
└─────────────────────────────────────────────────────────────────────┘
                                    ↓
┌─────────────────────────────────────────────────────────────────────┐
│ Insert probe into selected medication container, where direction    │
│ and/or depth are optionally based on medication container data      │
│ and/or pill property data                                           │
│ 406                                                                 │
└─────────────────────────────────────────────────────────────────────┘
                                    ↓
┌─────────────────────────────────────────────────────────────────────┐
│ Apply suction, suction level optionally based on medication         │
│ container data and/or pill property data                            │
│ 408                                                                 │
└─────────────────────────────────────────────────────────────────────┘
                                    ↓
┌─────────────────────────────────────────────────────────────────────┐
│ Receive sensor signal/s                                             │
│ 410                                                                 │
└─────────────────────────────────────────────────────────────────────┘
                                    ↓
┌─────────────────────────────────────────────────────────────────────┐
│ Optionally, save sensor signal/s, optionally as pill property data  │
│ and/or medication container data                                    │
│ 412                                                                 │
└─────────────────────────────────────────────────────────────────────┘
                                    ↓
                                FIG. 4A
```

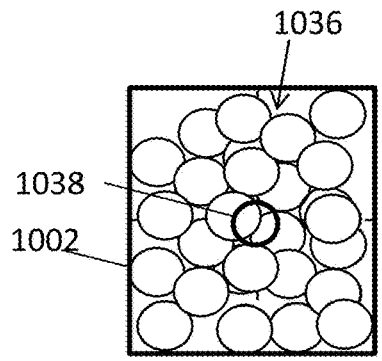
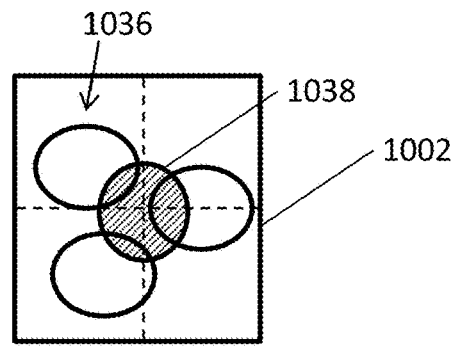
FIG. 10A
FIG. 10B
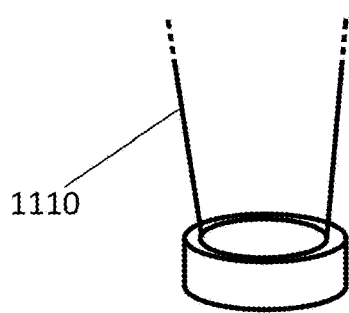
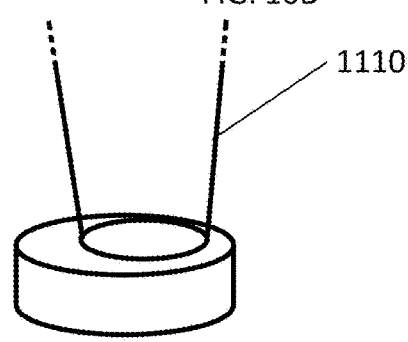
FIG. 11A
FIG. 11B
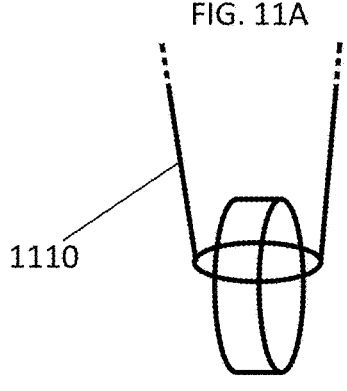
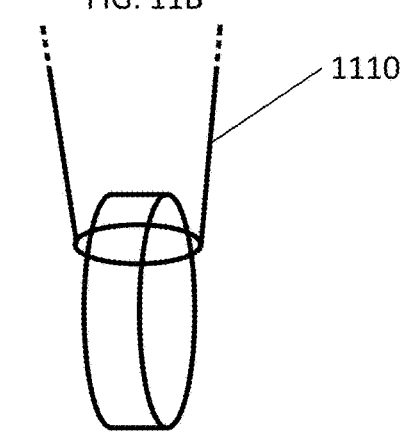
FIG. 11C
FIG. 11D
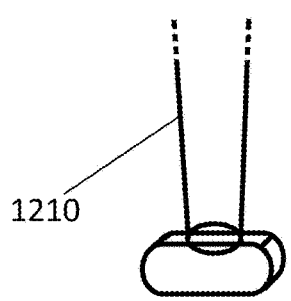
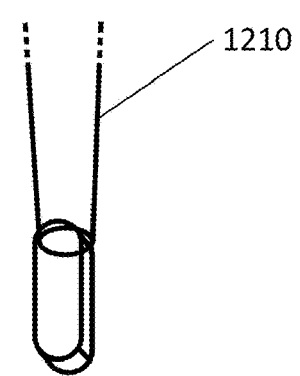
FIG. 12A
FIG. 12B

APPARATUSES AND METHODS FOR HANDLING PILLS WITHIN PHARMACEUTICAL DISPENSING DEVICES

RELATED APPLICATIONS

This application is a Continuation of U.S. patent application Ser. No. 16/737,943 filed on Jan. 9, 2020, which is a Continuation-in-Part (CIP) of U.S. patent application Ser. No. 16/430,456 filed on Jun. 4, 2019, now U.S. Pat. No. 10,964,154. The contents of the above applications are all incorporated by reference as if fully set forth herein in their entirety.

This application is also related to:

U.S. patent application Ser. No. 16/379,831 filed on Apr. 10, 2019,

U.S. patent application Ser. No. 16/379,835 filed on Apr. 10, 2019, and

U.S. patent application Ser. No. 16/559,716 filed on Sep. 4, 2019.

The contents of the above applications are all incorporated by reference as if fully set forth herein in their entirety.

FIELD AND BACKGROUND OF THE INVENTION

The present invention, in some embodiments thereof, relates to handling pills within a pharmaceutical dispensing device and, more particularly, but not exclusively, to extraction of pills from medication containers.

SUMMARY OF THE INVENTION

Following are examples of some embodiments of the invention. Features of one example may be combined with features of one or more other examples, unless expressly prohibited and form additional examples of some embodiments of the invention.

Example 1. A method of dispensing medication from a plurality of medication containers, using a dispensing system for collecting a medication dosage from a medication container comprising:

receiving a medication selection;

selecting a medication container, from said plurality of medication containers, based on said medication selection;

matching a collection protocol to be applied to said medication container including one or more parameter for control of said dispensing system; and dispensing said medication selection from said medication container according to said collection protocol.

Example 2. The method of Example 1, wherein said dispensing system comprises a probe, said method comprising: inserting said probe into said selected medication container; and collecting said medication selection with said probe.

Example 3. The method of Example 2, wherein said collecting comprises applying suction, according to said collection protocol.

Example 4. The method of Example 3, wherein said inserting comprises inserting said probe to an initial depth at an initial position, said initial depth and said initial position according to said collection protocol.

Example 5. The method of Example 4, wherein said collection protocol includes one more of:

one or more parameter based on medication data associated with said medication selection; and one or more parameter based on medication container data.

Example 6. The method of Example 5, wherein said medication data comprises a weight of a pill of said medication selection;

wherein said collection protocol comprises a suction parameter based on said weight.

Example 7. The method of Example 5, wherein said medication data comprises a least one dimension of a pill of medication selection; and wherein said collection protocol comprises a movement parameter based on at least one dimension.

Example 8. The method of Example 5, wherein said medication container data comprises at least one position within the container, of a previously successful pill extraction;

wherein said initial position is based on said at least one position.

Example 9. The method of Example 5, comprising receiving a measurement signal; and determining a quality of coupling of a pill to said probe, based on said measurement signal;

changing at least one parameter of said collection protocol if said determining indicates that quality of coupling is insufficient.

Example 10. The method of Example 9, wherein said at least one parameter comprises a position of said probe in said medication container.

Example 11. The method of Example 10, comprising:

measuring a proximity measurement signal of proximity of an opening of said probe to a pill; and wherein said changing comprises moving said probe to a position based on said proximity measurement signal.

Example 12. The method of Example 11, wherein said proximity measurement signal is a visual measurement signal.

Example 13. The method of Example 10, wherein said inserting comprises inserting said a probe in a first direction into said medication container to an initial depth at an initial position on a plane perpendicular to said first direction;

wherein said position is a position of said probe on said plane, said changing thereby changing a position of said probe.

Example 14. The method of Example 13, wherein said position is a step size in distance from said initial position, said step size depending on medication data and/or container data.

Example 15. The method of Example 12, wherein said medication data includes at least one pill dimension;

wherein said container data includes one or more historical successful extraction position.

Example 16. The method of Example 9, comprising repeating said determining and said changing until said determining indicates that said quality is sufficient.

Example 17. The method of Example 16, comprising removing said probe and said pill from said medication container.

Example 18. The method of Example 16, comprising saving a position of said probe when said quality is sufficient.

Example 19. The method of Example 9, wherein said changing comprises changing a suction level, based on medication data.

Example 20. The method of Example 19, wherein said medication data includes one or more of:

a pill weight;

historical successful suction levels.

Example 21. The method of Example 9, wherein said determining comprises one or more of:
  receiving a probe suction level measurement;
  receiving a weight measurement of said medication container; and
  receiving a weight measurement of said probe.

Example 22. The method of Example 13, wherein said initial depth is based on a fullness level of said medication container.

Example 23. The method of Example 22, wherein said fullness is determined using one or more of:
  a value received from a memory; and
  a measurement signal comprising one or more of:
  a weight measurement; and
  a proximity detection measurement.

Example 24. The method of Example 13, wherein said inserting comprises selecting a probe based on said pill property data.

Example 25. The method of Example 9, wherein said determining comprises:
  reducing suction for a time period; and
  comparing said measurement signal before said time period and after said time period.

Example 26. The method of Example 2, wherein said medication selection comprises a desired number of pills, said method comprising:
  receiving a measurement signal;
  determining a number of pills coupled to said probe, based on said measurement signal;
  changing at least one parameter of said collection protocol if said determining indicates that the number of pills coupled is less or more than said desired number of pills.

Example 27. The method of Example 26, wherein said determining comprises:
  reducing suction for a time period; and
  comparing said measurement signal before said time period and after said time period.

Example 28. A dispensing system for collecting a medication dosage from a medication container comprising:
  a suction source;
  a probe connected to said suction source and configured to apply suction from said suction source at a probe opening;
  one or more actuator configured to move said probe to said medication container and into sufficient proximity to said medication dose to couple said medication dose to said probe under said suction at said probe opening.

Example 29. The dispensing system of Example 28, wherein said one or more actuator is configured to move said probe into said medication container.

Example 30. The dispensing system of Example 29, wherein said one or more actuator is configured to move said probe within said medication container.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as collecting dental measurements, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 4A-4B is a detailed method of medication dispensing, according to some embodiments of the invention;

FIGS. 10A-10B are simplified schematic top views of a container containing pills with a cross section of a probe at the probe tip superimposed on the top view, according to some embodiments of the invention;

FIGS. 11A-11D are simplified schematics of a probe coupled to pills, according to some embodiments of the invention;

FIGS. 12A-12B are simplified schematics of a probe coupled to pills, according to some embodiments of the invention;

DESCRIPTION OF SPECIFIC EMBODIMENTS OF THE INVENTION

Figure 1A:
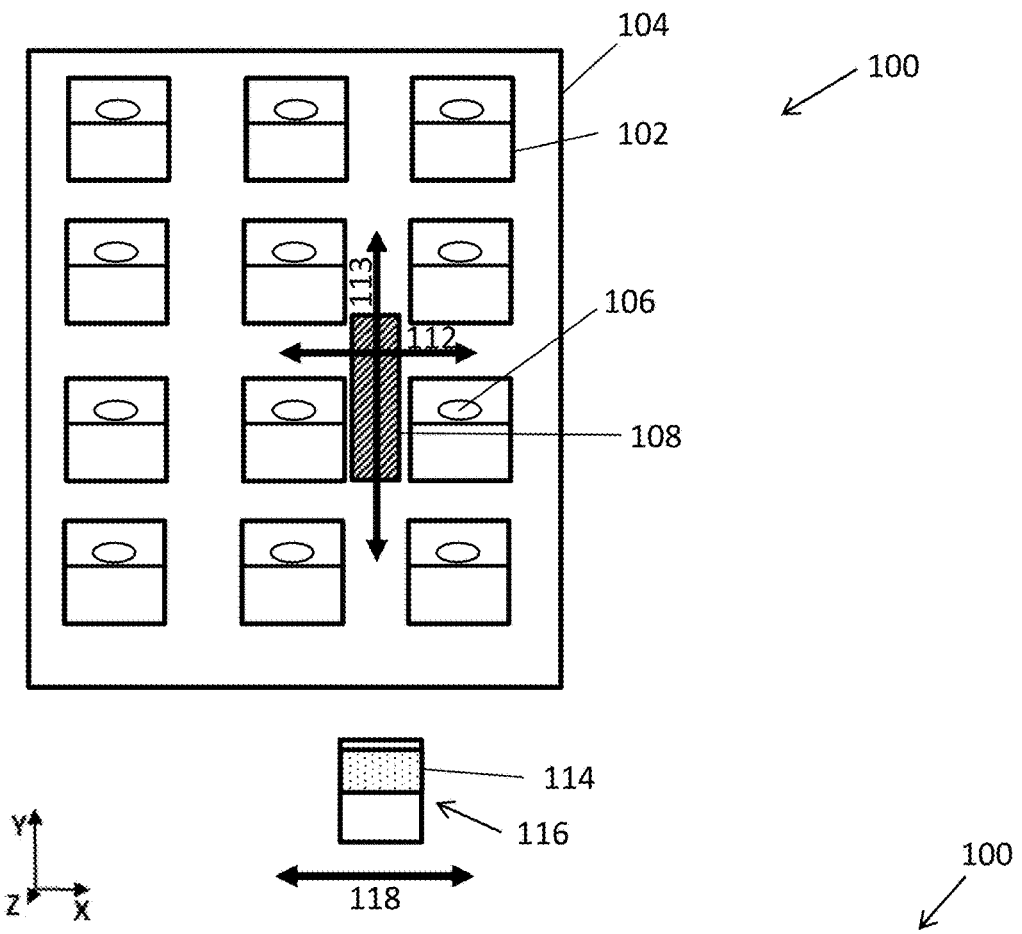
FIG. 1A is a simplified schematic front view of a dispensing system, according to some embodiments of the invention.

The present invention, in some embodiments thereof, relates to handling pills within a pharmaceutical dispensing device and, more particularly, but not exclusively, to extraction of pills from medication containers.

Overview

A broad aspect of some embodiments of the invention relates to extraction of pills (or medication unit/s) from medication containers where extraction is tailored to parameter's of the particular pill and/or condition/s of the medication container. In some embodiments, a probe is inserted into a medication container, couples a pill to the probe, e.g. by suction at a probe opening, and then extracts the pill by removing the probe.

An aspect of some embodiments of the invention relates to extracting a pill using a collection protocol, which is matched to the pill and/or the conditions of the pill to be extracted.

In some embodiments, a collection protocol is a pick-up protocol where a pill is picked up by a probe inserted into a medication container. In some embodiments, a medication unit (e.g. pill) is collected using a different collection technique, for example, by opening a valve at a base of the medication container and allowing a pill to exit through the valve e.g. under gravity.

In some embodiments, one or more pick-up protocol parameter is based on one or more pill property and/or one or more medication container condition. In some embodiments, matching includes selecting a pick-up protocol. In some embodiments, matching includes generating a pick-up protocol. In some embodiments, matching comprises adjusting one or more parameter in a pick-up protocol.

In some embodiments, pill properties include one or more constant property, for example, one or more of; pill size, pill shape, pill weight, pill material properties (e.g. hardness), and calibration data.

Alternatively or additionally, in some embodiments, pill properties include one or more dynamic property, for example, a desired number of pills, historical data on successful extraction e.g. suction level, probe size, step size.

In some embodiments, medication container conditions include constant parameters, for example, internal size and/or shape of the medication container.

Alternatively or additionally, in some embodiments, medication container conditions include dynamic conditions, for example, a fullness of the medication container. Where fullness, in some embodiments, is defined as a distance from a top level of the container to a level of the pills within the container or is defined a height from a base of the container to the level of pills within the container.

In some embodiments, fullness distance/s are directly measured. In some embodiments, fullness distance/s are determined from measurement (e.g. from weight sensor measurements) and/or determined (e.g. from historical extraction data).

In some embodiments, modifiable parameter/s of a pick-up protocol include parameter/s related to one or more initial conditions of the probe, for example, an initial position that the probe is inserted to and/or an initial suction level applied at the probe and/or a type of probe to be used.

In some embodiments, an initial suction level is selected to be a minimum level of vacuum required e.g. to couple a particular pill to the probe e.g. based on a weight of the pill to be extracted. For example, in some embodiments, a pick-up protocol suction level is based on a weight of the pill to be extracted, higher suction (lower pressure) being applied at the probe to extract heavier pill/s. A potential advantage of applying minimal suction (e.g. for a particular pill) is reduction in damage to pills and/or prevention of coupling more than a desired number of pills to the probe.

In some embodiments, an initial position of a probe is selected based on a size of the medication container and/or fullness of the medication container and/or historical position within the container of one or more previous successful pill extractions e.g. position of a previous 1, or 2, or 3, or 4, or 1-10, or lower or higher or intermediate numbers of previous successful extractions. In an exemplary embodiment, a probe is inserted into a medication container to a depth selected based on the fullness of the medication container and/or a positon of the probe in a plane perpendicular to a depth direction of the container is based on positions of previous successful extractions.

In some embodiments, whether a pill is coupled to the probe is determined from one or more sensor measurement. For example, from one or more weight sensor, (e.g. a weight of the medication container reduces upon successful coupling and/or a weight of the probe increases upon successful coupling) and/or from a suction sensor (e.g. measured suction at the probe reduces upon coupling).

In some embodiments, during extraction of a pill from a medication container, one or more pick-up protocol parameter is adjusted. The adjustment, in some embodiments, is based on feedback received during extraction.

For example, in some embodiments, a step size is changed.

For example, in some embodiments, suction levels applied at the probe to couple a pill to the probe by suction are changed, for example, increased after failure to couple a pill.

In some embodiments, a pick-up protocol specifies change/s, which are, for example, made upon unsuccessful pill coupling to the probe. For example, changes to positon of the probe (e.g. step size for a change of position of the probe) and/or change/s to suction level at the probe.

For example in some embodiments, a probe inserted into the medication container is moved within the container in one or more direction, until a pill is successfully extracted. In some embodiments, the probe is moved by a step size defined by the pick-up protocol.

In some embodiments, a pick-up protocol specifies an order of changes, which are made upon failure to couple a pill to the probe.

For example, in some embodiments, suction is changed first, and only upon failure of one or more suction level different to an initial suction level (e.g. a plurality of suction levels up to a maximum suction level, which, in some embodiments, depends on pill parameter/s and/or container parameter/s) is the probe moved.

Alternatively, in some embodiments, the probe is moved one or more time before suction levels are changed.

In some embodiments, sensor signals are used to change the pick-up protocol. For example, in some embodiments, proximity of the probe to pill/s is identified from sensor measurement/s, for example visual sensor measurement/s (e.g. imager measurements) and/or proximity sensor measurement/s. In some embodiments, movement of the probe is based on the identified proximity.

In some embodiments, data regarding successful extraction of pills is used to update parameter/s of a pick-up protocol. For example, in some embodiments, a pick-up protocol initially has one or more parameter based on one or more pill property and/or container condition. During extraction from the container, using the pick-up protocol, successful pick-up data (e.g. suction level, position) is used to adjust the pick-up protocol. For example, an initial suction level is defined by a pill weight. Successful coupling is achieved with higher suction levels and the pick-up protocol is adjusted so that the initial suction level, for the pill type and/or for the particular container is higher.

In some embodiments, pick-up protocols are generated and/or adjusted during calibration. For example, in some embodiments, a new pill is introduced to the system. Optionally, data regarding the new pill (e.g., "pill properties" e.g. pill size, weight) are inputted into the memory and optionally used to generate the pick-up protocol.

Alternatively or additionally, the pick-up protocol is generated and/or adjusted based on test routines where pills are extracted using pick-up protocols e.g. different suction levels and/or movement parameters (e.g. step size).

In some embodiments, a range of different suction levels and/or step sizes are tested, data for successful coupling of pills is used to generate pick-up protocol/s. In some embodiments, a minimum effective suction level and/or minimum effective step size are determined in calibration and optionally used in a pick-up protocol for the new pill type.

In some embodiments, a pick-up protocol includes selecting a probe from a plurality of probes. In some embodiments, a pill is coupled to a probe at an opening of the probe. In some embodiments, the opening is located at a tip of the probe, and within this document, the term "probe tip" is used interchangeably with the term probe opening and is intended to cover embodiment where the opening is not located at a tip of the probe. In some embodiments, probe tip area is selected based on pill properties, for example, in some embodiments a size of a tip area is based on pill dimensions e.g. larger pill, larger tip. In some embodiments, probe tip curvature is based on pill curvature, a potential advantage being improved sealing between the tip and the probe for improved coupling.

In some embodiments, a probe has a perforated tip (e.g., the tip is covered in a mesh). A potential advantage of a perforated tip is the ability to couple more than one pill to the tip. In some embodiments, the tip size is larger than the pill, so that the pill would be sucked into the tip if the tip did not have a cover (e.g. mesh cover). In some embodiments, the perforated tip cover is used to extract more than one pill where a sensor (e.g. weight sensor) is used to determine the number of coupled pills to the tip.

In some embodiments, a probe is configured to couple to a range of dimensioned pills. For example, in some embodiments, a probe opening includes a tapered inlet, pills entering into the probe opening, at a depth associated with dimensions of the pills.

In some embodiments, a probe is selected to match geometry of a pill to be collected, for example, a cross section of an opening of a probe is selected based on the pill shape. For example, in some embodiments, ovalic shape pills are collected using a probe tip with ovalic cross section, in some embodiments, spherical pills are collected using a probe tip with circular cross section.

In some embodiments, the probe is configured to impact the container and/or pills with low force during movement of the probe. A potential advantage being low damage to the container and/or pills. In some embodiments, the probe is soft e.g. made of softer material (e.g. silicone rubber) than that of the pills to be extracted. In some embodiments the probe is deformable (e.g. elastically) in one or more direction.

Throughout this document, the term "pill" has been used. It should be understood that the term is intended to cover all to cover all discrete medication units. Furthermore, in some embodiments, the probe is used to extract fluid medication (e.g. liquid, powder, granules) where, in some embodiments, the fluid medication is held within the probe. In some embodiments, a suction level is selected to extract the required amount of fluid medication. In some embodiments, feedback as to whether the correct amount of fluid medication has been collected is provided by a probe weight sensor and/or a container weight sensor.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Pharmaceutical Dispensing Systems

FIG. 1A is a simplified schematic front view of a dispensing system 100, according to some embodiments of the invention.

Figure 1B:
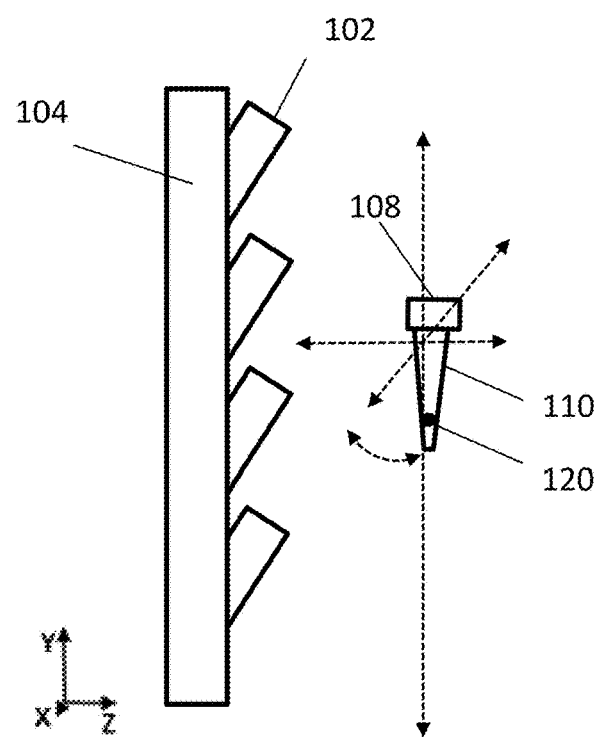
FIG. 1B is a simplified schematic side view of a dispensing system, according to some embodiments of the invention.

FIG. 1B is a simplified schematic side view of a dispensing system 100, according to some embodiments of the invention.

In some embodiments, FIG. 1B is a side view of the dispensing system of FIG. 1A.

In some embodiments, dispensing system 100 includes at least one container 102. In some embodiments, system 100 includes a plurality of containers 102. In an exemplary embodiment, containers are arranged in a vertical array where containers are arranged one above each other (e.g. stacked) e.g. rows of containers are arranged vertically. In some embodiments, the containers are attached to and/or part of a medications panel 104. In some embodiments, each container includes an opening 106 through which pills are extracted.

In some embodiments, a container has an internal shape configured to control movement of pills within the container e.g. as the pills are inserted (e.g. poured into the container) and/or movement of remaining pills as pills are extracted. In some embodiments, a container has a shape with a tapered base, pills flowing in a direction of the taper. In some embodiments, the container is shaped to orientate and/or locate pills (orient e.g. non-spherical pills), for example, a container including a plurality of indentations where pill/s are configured to move into the indentations. In some embodiments, non-spherical pills are orientated so that a larger and/or largest face of the pill is presented in a direction of the probe, potentially reducing a number of pick-up attempts required to extract a pill, as the probe, potentially couples more effectively to a larger pill face. In some embodiments, pills are positioned in known locations e.g. by shaping of the pill container, potentially reducing the number of pick-up attempts required as, in some embodiments, the probe is placed in positions where pills are expected (and/or likely to be located). In some embodiments, dispensing system 100 includes a dispensing head 108, which extracts pill/s from the container/s. In some embodiments, the system includes one or more actuator (not illustrated) which is configured to move (e.g. as illustrated by arrows 112, 113) the dispensing head to a region of a selected container.

In some embodiments, dispensing head 108 includes a probe 110 (and/or an interface for attachment thereto of a probe). Where probe 110, in some embodiments, is sized and/or shaped for insertion into one or more container through the respective container opening/s.

In some embodiments, probe 110 is inserted into a container by movement of the dispensing head e.g. the dispensing head moved by one or more of the same actuators which move the head to a region of a selected container.

In some embodiments, the system includes a first set of actuators, which move the dispensing head to a region of a selected medication container. In some embodiments, additional actuator/s perform fine movement of the probe with respect to the container. For example, in some embodiments, the probe is moved with respect to the dispensing head.

In some embodiments, the dispensing head includes a gripper configured to connect the dispensing head to a probe where, in some embodiments, the system includes a plurality of probes.

In some embodiments, suction is applied at the probe to couple a pill (e.g. pill) to the probe. In some embodiments, suction is applied by a suction source (e.g. suction) pump fluidly coupled to the probe e.g. fluidly coupled to one or more opening of the probe.

In some embodiments, pill/s are dropped by the gripper and probe after extraction from a container into a receptacle 114. In some embodiments, receptacle 114 is held by a carrier 116, which, in some embodiments, moves 118 to position receptacle 114 underneath the dispensing head. In some embodiments, receptacle 114 is an open envelope.

In some embodiments, the probe includes (and/or is connected to) one or more sensor 120. In some embodiments, sensor 120 provides feedback as to suitability of position of the probe for extracting a pill for example proximity of the probe to a pill. In some embodiments, sensor 120 comprises an imager and/or a force sensor.

In some embodiments, an imager (e.g. which provides feedback used in positioning the probe) is disposed within a suction channel of a probe, for example, the imager collecting visual data (e.g. images) of pills from within the channel. Alternatively or additionally, in some embodiments, an imager is disposed on an outer surface of the probe.

Figure 2:
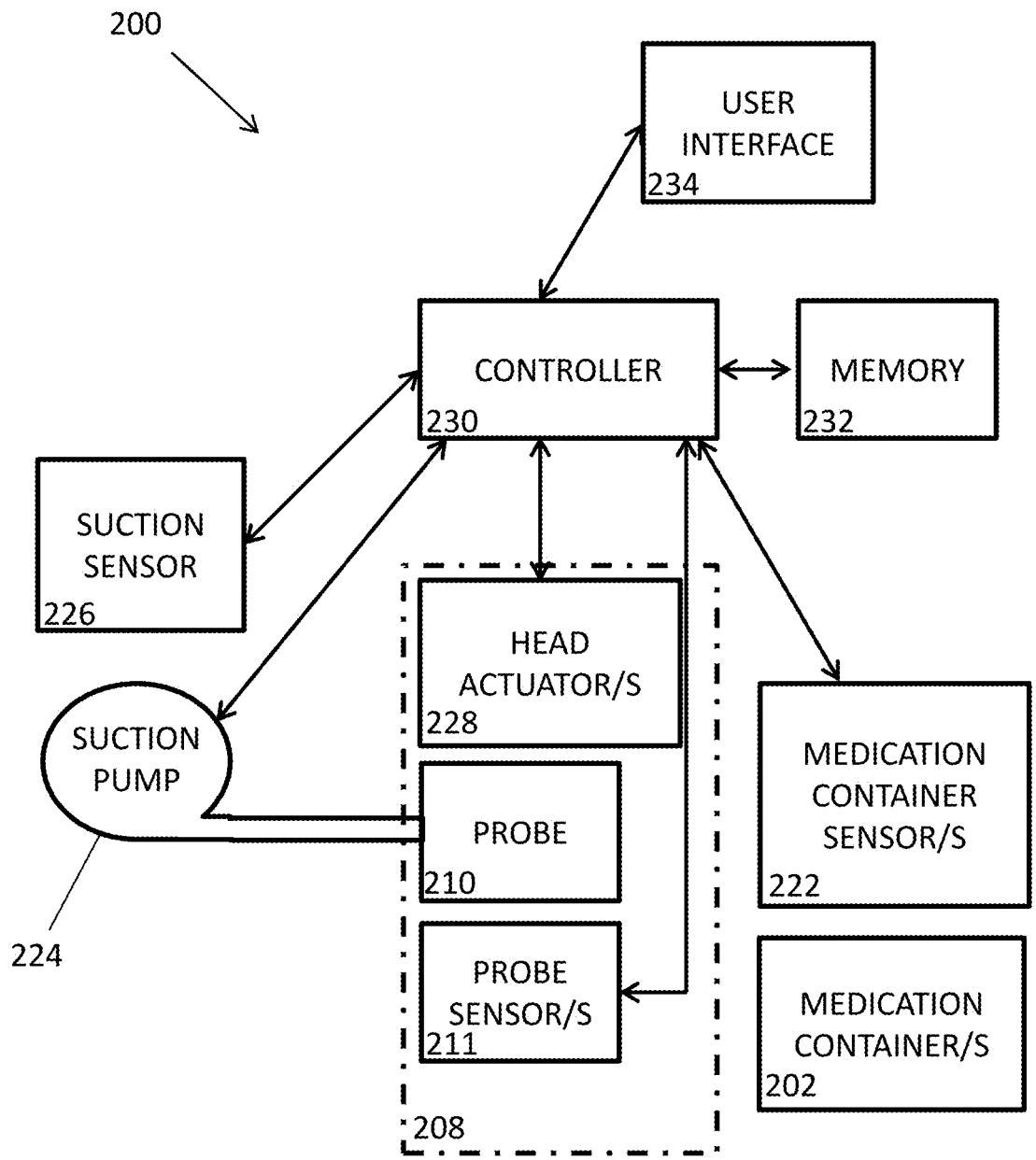
FIG. 2 is a simplified schematic of a pharmaceutical dispensing system, according to some embodiments of the invention.

FIG. 2 is a simplified schematic of a pharmaceutical dispensing system 200, according to some embodiments of the invention.

In some embodiments, system 200 includes at least one medication container 202, and in some embodiments, a plurality of medication containers e.g. an array of medication containers (e.g. including one or more feature as described and/or illustrated regarding containers 102 FIGS. 1A-B).

In some embodiments, system 200 includes one or more medication container sensor 222. In some embodiments, a medication container sensor senses weight of one or more medication container.

In some embodiments, system includes a probe 210 for collecting medication from medication container/s 202. In some embodiments, probe 210 collects medication by application of negative pressure at an opening of the probe (e.g. at an opening at a tip of the probe). Where, in some embodiments, negative pressure is supplied by a suction pump 224.

In some embodiments, system 200 includes more than one type of probe and, in some embodiments, a probe is selected for extraction of a particular medication and/or from a particular container. In some embodiments, system 200 includes a plurality of probes with different sized tips.

In some embodiments, a suction sensor 226 measures suction applied by suction pump 224 and/or measures suction at probe 210. For example, in some embodiments, suction measured by suction sensor 226 reduces once a pill (e.g. pill) is coupled to probe 210 by suction.

In some embodiments, system 200 includes one or more actuator 228, which move probe 210 with respect to the medication container/s. In some embodiments, one or more actuator moves probe 210 into a medication container and/or moves the probe within the medication container and/or with respect to the medication container.

In some embodiments, system 200 includes a controller 230. In some embodiments, controller sends instructions to suction pump 224 and/or head actuators 228 to control extraction of medication from medication container/s 202.

For example, in some embodiments, controller 230 receives data (e.g. a medication selection e.g. a collection protocol) and generates and/or sends control signals to actuator/s e.g. actuator/s configured to move the probe and/or actuator/s which control suction at the suction pump.

In some embodiments, system 200 includes one or memory 232. In some embodiments, memory 232 is hosted within the system. Alternatively or additionally, in some embodiments memory 232 includes memory external to the system.

In some embodiments, system 200 includes one or more user interface 234. In some embodiments, a user enters information into the user interface e.g. a medication request for medication to be dispensed e.g. regarding a medication schedule for a particular patient.

In some embodiments, controller 230 generates the instructions based on sensor signal/s e.g. from one or more of sensors 226, 222, 211. Alternatively or additionally, in some embodiments, controller instructions are generated based on data retrieved from a memory 232 and/or instructions inputted into a user interface 234.

Exemplary Medication Dispensing

Figure 3:
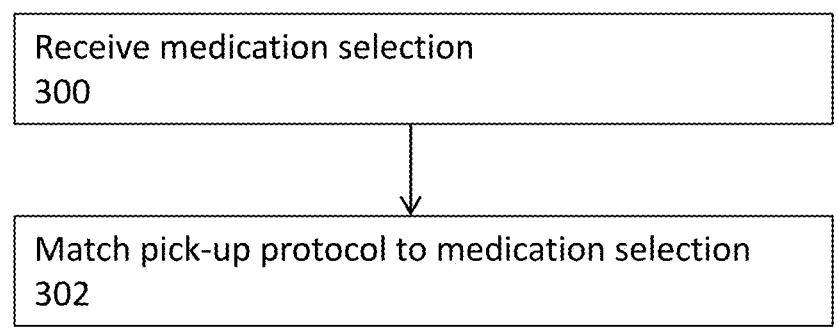
FIG. 3 is a flow chart of a method of medication dispensing, according to some embodiments of the invention.

FIG. 3 is a flow chart of a method of medication dispensing, according to some embodiments of the invention.

At 300, in some embodiments, a desired medication selection is received. E.g. including one or more feature as described regarding step 400, FIG. 4A.

At 302, in some embodiments, a pick-up protocol is matched to the medication selection.

Figure 4B:
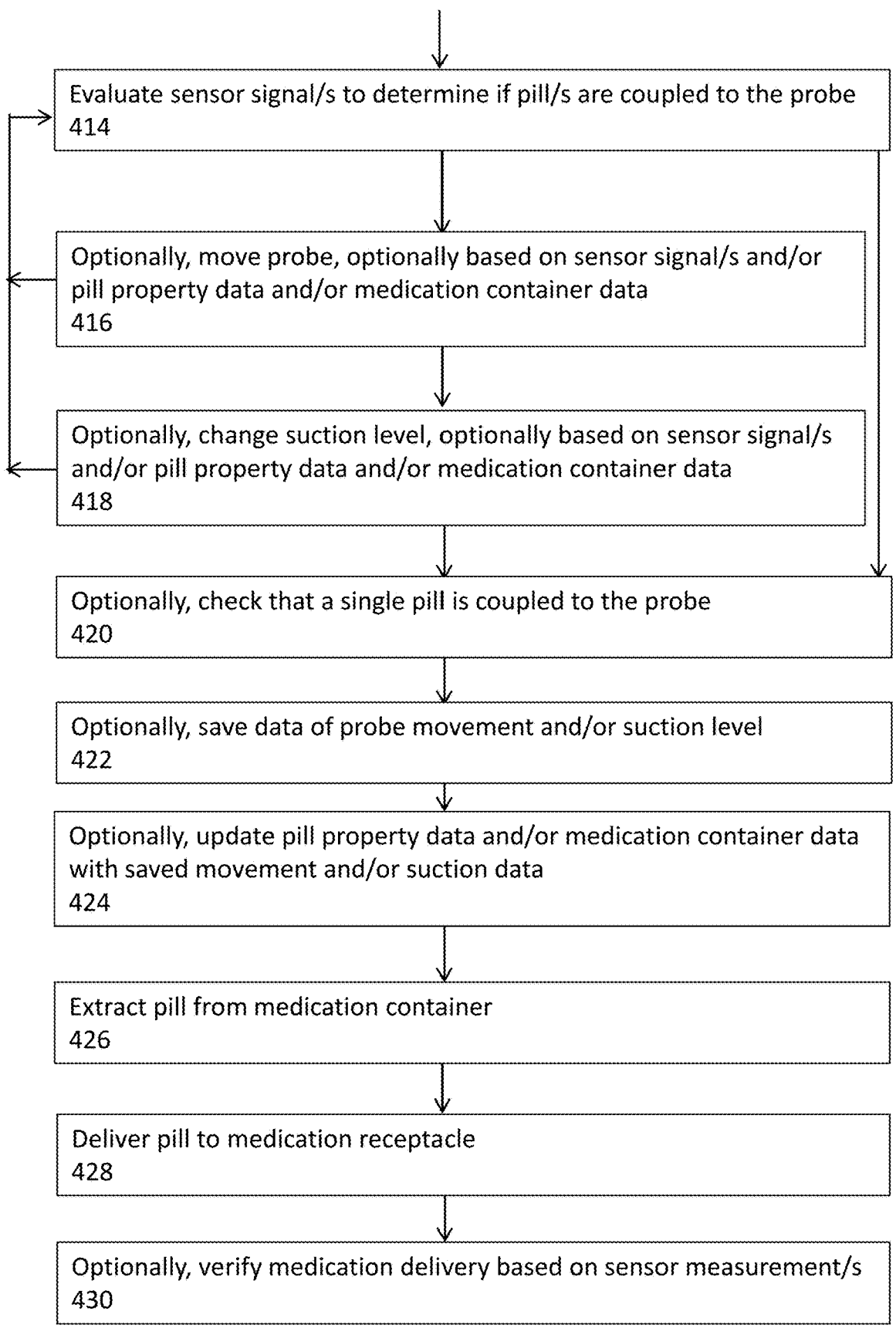

FIGS. 4A-4B is a detailed method of medication dispensing, according to some embodiments of the invention.

At 400, in some embodiments, a medication request is received. In some embodiments, the request includes a medication selection including a type of medication and/or a number of pills (e.g. number of pills).

In some embodiments, the request is received from a user interface. For example, the medication request is inputted by a user through the user interface (user interface e.g. including one or more feature as described and/or illustrated regarding user interface 228 FIG. 2). In some embodiments, a user inputs one or more identifier e.g. a patient identifier and/or a time identifier and/or a ward identifier and from the identifier/s the controller identifies (e.g. from a memory e.g. a look-up table) a medication request. Alternatively or additionally, in some embodiments, the request is automatically generated e.g. based on previous inputs and/or data received e.g. from an external source.

At 402, in some embodiments, a medication container is selected, based on the received medication request. For example, medication container holding the desired medication is selected e.g. using a memory (e.g. memory 226 FIG. 2).

In some embodiments, the system selects a container from more than one possible container, optionally based on container parameters e.g. fullness of the respective containers, e.g. location of the container/s e.g. expiry date of medication in a container. There is more than one possible container, for example, in situations where more than one container houses a same medication and/or when a dose of medication may be made up using different combinations of medication from different containers (e.g. a patient dosage is 100 mg and a container including 100 mg pills may be selected or two pills from a container including 50 mg pills may be selected).

At 403, optionally, pill property data and/or medication container data is received e.g. from a memory (e.g. memory 226 FIG. 2).

In some embodiments, pill property data (also herein termed "pill properties") includes one or more of; historical data on successful suction level/s for extraction of the medication, historical data on successful step size for movements in a pick-up protocol, size, shape, weight, material properties (e.g. hardness) of the medication.

In some embodiments, medication container data includes one or more of internal dimension/s of the container, a fullness height and/or depth and/or weight of the container, and/or historical data on position of previous pill extraction/s.

At 404, optionally, a probe is selected, for example, from a plurality of probes. In some embodiments, probe selection is based on pill property data e.g. size and/or shape of the medication.

For example, in some embodiments, a probe is selected for extraction of a pill, where a dimension of the probe (e.g. probe tip e.g. cross sectional inner dimension of the probe tip e.g. maximum dimension and/or minimum dimension and/or average dimension) is based on one or more dimension of the pill to be extracted e.g. a pill maximum dimension and/or a pill minimum dimension and/or a pill average dimension (e.g. pill dimensions as defined regarding step 416 of FIG. 4B).

Figure 6A:
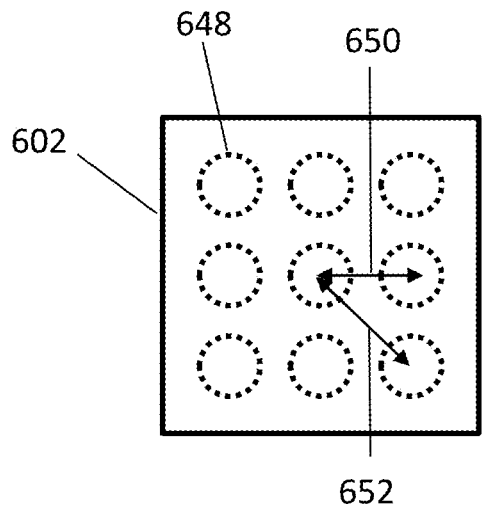
FIGS. 6A-6C are simplified schematics illustrating possible probe locations within a medication container, according to some embodiments of the invention.
Figure 6B:
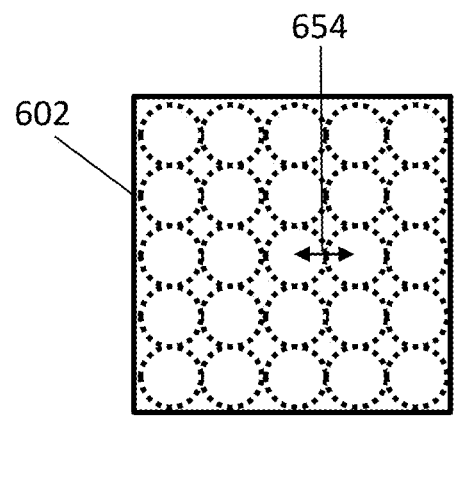
Figure 6C:
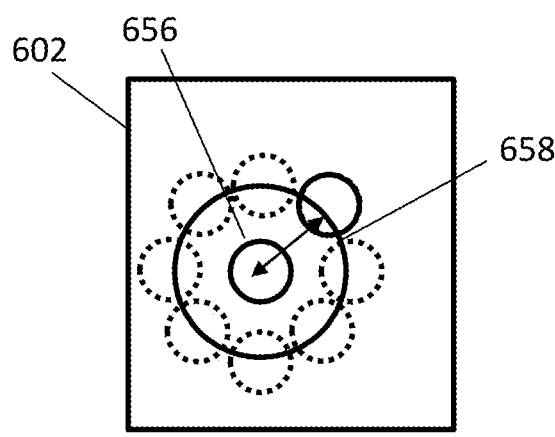
Figure 6D:
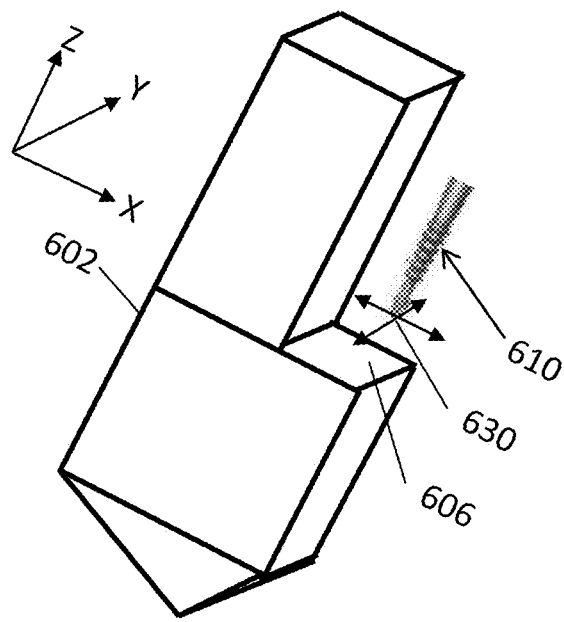
FIG. 6D is a simplified schematic of a medication container and probe, according to some embodiments of the invention.

At 406, in some embodiments, a probe is inserted into the selected medication container e.g. through an opening in the container (e.g. opening 106 FIG. 1A, opening 606 FIG. 6D). In some embodiments, direction and/or depth of insertion, are based on medication container and/or pill property data. For example, in some embodiments, an initial depth of insertion of the probe is based on a fullness level of the container. For example, in some embodiments, an initial position of insertion of the probe is based on position/s of successful previous pill extraction/s.

At 408, in some embodiments, suction is applied at the probe. In some embodiments, a suction level is based on medication container data and/or pill property data. For example, in some embodiments, higher suction is applied for extraction of large and/or heavy medication.

At 410, in some embodiments, one or more sensor signal is received. For example, suction level at the probe, for example, weight of the medication container. For example, visual sensor data from within the medication container e.g. data from a visual sensor at the probe (e.g. sensor 120 FIG. 1B). For example, force sensor data e.g. from a force sensor at the probe (e.g. sensor 120 FIG. 1B).

At 412, optionally, in some embodiments, sensor signal/s are saved. For example, as pill property data and/or medication container data.

At 414, in some embodiments, sensor signal/s are evaluated to determine if pill/s are coupled to the probe. Where, for example, in some embodiments, a measured reduction in suction at the probe is compared with a threshold to determine if a pill is coupled to the probe.

In some embodiments, different pills have different thresholds. For example, in some embodiments, the threshold depends on the pill shape and/or weight.

In some embodiments, a quality of coupling of the pill to the probe is determined.

In some embodiments, for example, where the pill shape is not symmetrical, suction level, in some embodiments, indicates orientation of the pill with respect to the probe.

Alternatively, or additionally, in some embodiments, measured weight of a medication container is compared with a historical weight of the container to determine if a pill is coupled to the probe.

In some embodiments, sensor signal/s are evaluated to determine if a correct number of pills are coupled to the probe. For example, only one, or more than one, where the medication request includes more than one pill to be extracted from the same container. In some embodiments, a weight sensor is used to provide feedback as to the number of pills coupled to the probe.

At 416, in some embodiments, if it is determined that coupling of a desired number of pill/s to the probe has failed, the probe is moved.

In some embodiments, movement of the probe is discrete where, for example, while the probe is moved, suction is stopped and reapplied once the probe has been repositioned, step 414 being performed, in some embodiments, at each repositioning. Alternatively, in some embodiments, suction is applied continuously as the probe is moved.

In some embodiments, movement of the probe is based on one or more pill property. For example, in some embodiments, movement of the probe in a direction is by a step size, where, in some embodiments, the step size is related to one or more dimension of the pill.

For example, in some embodiments, step size is based on average x/y/z dimensions of a pill to be extracted.

For example, in some embodiments, where a minimum volume occupied by a pill is defined by a volume a*b*c, the step size is 0.1*min(a,b,c)–10*max(a,b,c),
or 0.2*min(a,b,c)–5*max(a,b,c),
or 0.5*min(a,b,c)–2*max(a,b,c),
or lower or higher or intermediate values or ranges.

Where min(a,b,c), a minimum pill dimension, denotes the minimum of a, b, and c. Where max(a,b,c), a maximum pill dimension, denotes the maximum of a, b, and c.

In an exemplary embodiment, a step size is about an average pill dimension, an average of dimensions a, b, and c; average(a,b,c).

In some embodiments, the step size is the same for both increase in depth into the container (e.g. z direction illustrated in FIG. 6D) and lateral movement (movement within x-y plane as illustrated in FIG. 6D), within the container.

In some embodiments, before the probe is moved laterally (perpendicular to a depth direction) the probe is lifted (depth is reduced), for example, movement as illustrated in FIGS. 8A-E. A potential advantage being reduced likelihood of collision of the probe with pill/s.

Alternatively, in some embodiments lateral movement of the probe is performed without raising the probe beforehand, for example, movement as illustrated in FIGS. 7A-D.

In some embodiments, steps 414 and 416 are performed until it is determined that the desired number of pills are coupled to the probe.

In some embodiments, the probe is prevented from collision with pill/s, for example, using one or more sensor. For example, in some embodiments, a proximity sensor signal and/or a force sensor is evaluated and, if proximity of the probe reduces to below a threshold and/or a sensed force is above a threshold, probe movement is changed and/or ceased.

At 418, in some embodiments, if it is determined that coupling of a desired number of pill/s to the probe has failed, a suction level is changed. For example, in some embodiments, suction is increased.

In some embodiments, steps 416 and 418 are alternated.

In some embodiments, an order of steps 414 and 416 is reversed, for example, suction levels are first changed and then the probe is moved.

In some embodiments, several suction levels are attempted (e.g. with breaks in suction in between) before the probe is moved.

In some embodiments, several movements of the probe are performed before the suction level is changed.

In an exemplary embodiment, if, at a given position extraction with the initial suction level fails, the suction level is first changed, for example increased by 10-500%, or 50-300%, or up to 200%, or by about 200%, or lower or higher or intermediate ranges or percentages of the initial suction level.

Figure 5:
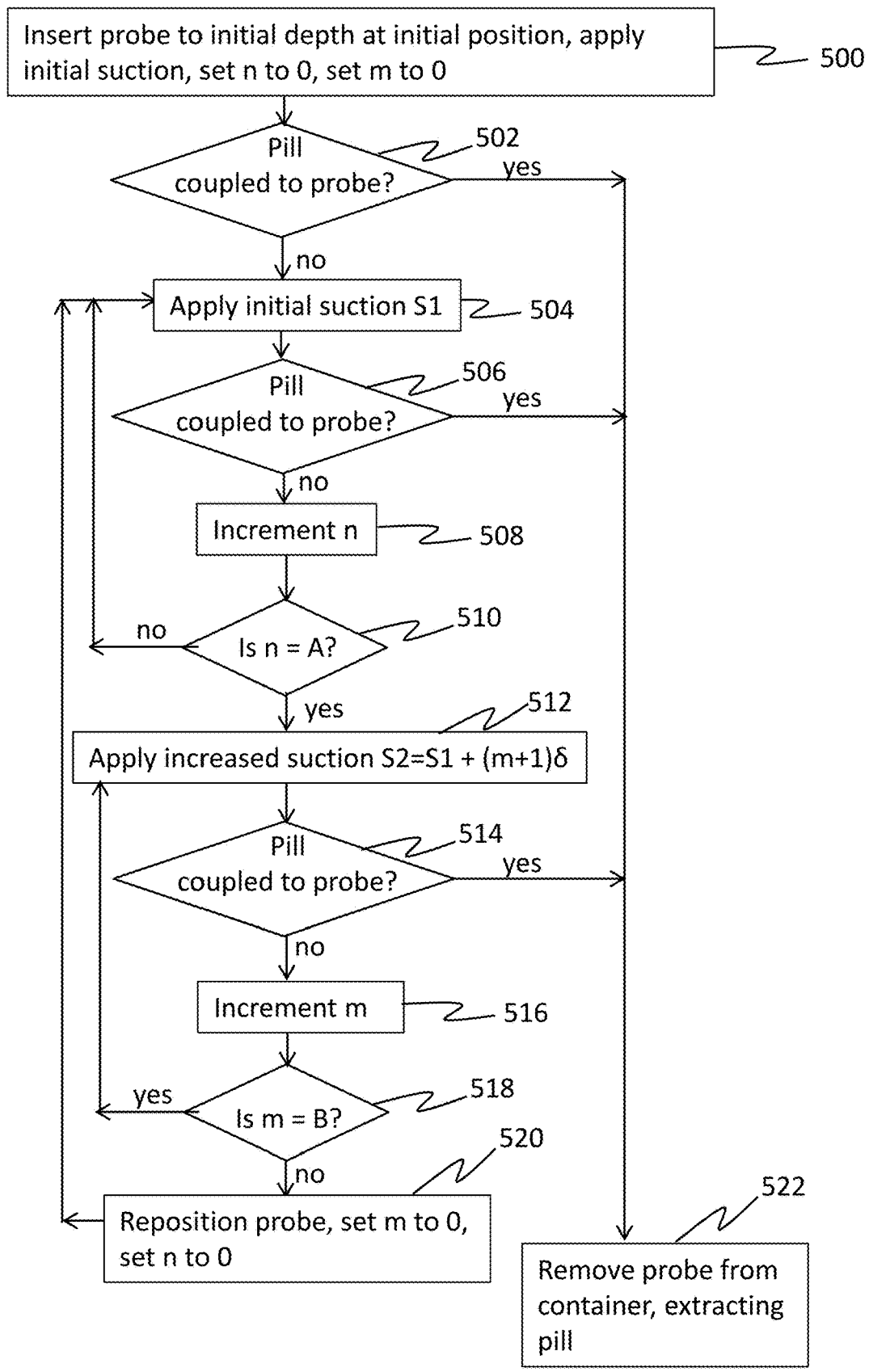
FIG. 5 is a flow chart of a pick-up protocol method of pill extraction, according to some embodiments of the invention.

FIG. 5, described in detail below, illustrates an exemplary pick-up protocol for changing suction and position of the probe.

At 420, optionally, in some embodiments, the system checks that a single pill is coupled to the probe. In some embodiments, the probe tip is sufficiently large and/or suction is sufficiently high that it is possible to couple more than one pill to the probe. In some embodiments, a sensor (e.g. weight sensor) is used to determine the number of coupled pills. Alternatively or additionally (e.g. when too many pills are coupled) to sensor feedback, in some embodiments, applied suction is reduced or ceased e.g. briefly. In some embodiments, after the change in suction, pill/s less securely coupled decouple from the probe and fall (e.g. back into the medication container). In some embodiments, a cessation (or reduction) in applied suction is for less than a second, or for 1-500 mS, or for 1-100 mS, or for 5-50 mS, or for lower or higher or intermediate times or ranges.

In some embodiments, a duration of cessation (or reduction) in suction is tailored to the specific pill. In some embodiments, the duration is based on a weight and/or size and/or shape of the pill.

In some embodiments, excess (e.g. of medication request) pill/s are decoupled by subjecting the probe to a shock, for example by banging the probe e.g. on the side of the medication container.

At 422, optionally, in some embodiments, data of probe movement and/or suction level is saved, for example in a memory (e.g. memory 232 FIG. 2).

At 424, optionally, in some embodiments, pill property data and/or medication container data is updated with saved movement and/or suction data.

At 426, in some embodiments, when it is determined that coupling of a desired number of pill/s to the probe has succeeded, the probe is moved out of the container (e.g. though the container opening) extracting the pill/s coupled to the probe.

At 428, the extracted pill/s are delivered e.g. to a medication receptacle (e.g. receptacle 114 FIG. 1A). For example, by reducing suction at the probe and allowing the pill/s to fall into the medication receptacle. In some embodiments, positive pressure is applied to de-couple the pill from the probe. For example, upon measurement signal/s (e.g. weight measurement of the receptacle) indicating that the pill is still coupled to the probe.

At 430, in some embodiments, delivery of pill/s is verified, for example, using weight sensor measurement at the delivery receptacle.

FIG. 5 is a flow chart of a pick-up protocol method of pill extraction, according to some embodiments of the invention.

FIG. 5 illustrates an embodiment where, until pill coupling is successful, an initial suction, S 1, is applied A times before suction is increased.

In some embodiments, the initial suction level is based on historically successful suction level/s for the pill type and/or for the selected container. In some embodiments, S1 is the level of suction applied during the previous extraction from the container.

Increasing suction S2=S1+(m+1)δ is then applied B times and then the probe is repositioned, the process restarting with the initial suction level S1. Where, in some embodiments, the illustrated order of steps and S1, S2, A, B, δ are defined by the pick-up protocol.

Where, in some embodiments, B is one corresponding to a protocol where two suction levels are applied, S1 and S2. Where, in some embodiments, A=1 corresponding to a protocol where suction is immediately increased after an initial suction level fails.

At 500, in some embodiments, a probe is inserted to an initial depth (in a z direction) at an initial position (x-y plane perpendicular to the depth z direction) within a medication container and an initial suction level is applied at the probe. In some embodiments, counts n and/or m are set to zero.

In some embodiments, the initial depth is based on historically successful depth/s for the pill type and/or for the selected container. In some embodiments, the initial depth is the depth that the probe was inserted to for the previous extraction from the container.

At 502, in some embodiments, whether a pill has successfully been coupled to the probe or not (e.g. with initial conditions at step 500) is determined. For example, using measurement e.g. suction levels and/or weight sensor measurement.

If "yes", a pill has successfully been coupled at step 502, at 522, in some embodiments, the probe is removed from the container extracting the pill.

If "no", a pill has not been coupled to the probe at step 502, at 504, in some embodiments, the initial suction is re-applied A times.

After application of initial suction level S1 A times, at 514, an increased suction level, S2 which is δ larger than S1, on the first iteration (S2=S1+(m+1)δ), is applied.

At 514, in some embodiments, whether a pill has successfully been coupled to the probe or not is determined. For example, using measurement e.g. suction levels and/or weight sensor measurement.

If "yes" a pill has successfully been coupled to the probe at step 514, at 522, in some embodiments, the probe is removed from the container extracting the pill.

If "no" a pill has not successfully been coupled at step 514, at 516, in some embodiments, m is incremented and, at 510, in some embodiments, n is compared with B, a maximum number of suction increases, corresponding to a maximum suction level Smax=S1+(B+1)δ). B and/or Smax e.g. as defined within the pick-up protocol.

In some embodiments, if m is not equal to B (e.g. is less than B), then step 512 is repeated.

If m is equal to B, in some embodiments, at 520, the probe is repositioned, e.g. by a step size and, in some embodiments, n and/or m are reset to 0 and, in some embodiments, the process continues at step 504.

FIGS. 6A-6C are simplified schematics illustrating possible probe locations 638 within a medication container 602, according to some embodiments of the invention.

FIGS. 6A-6C, in some embodiments, illustrate possible positions of the probe. Probe positions illustrated with dashed lines. Where FIGS. 6A-6C illustrate probe positons e.g. in an x-y plane perpendicular to a depth direction of the container, e.g. corresponding to directions illustrated in FIG. 6D:

FIG. 6D is a simplified schematic of a medication container 602 and probe 610, according to some embodiments of the invention. In some embodiments, arrows 630 of FIG. 6D show possible degrees of freedom of movement of probe 610 in an x-y plane.

In some embodiments, possible probe locations form an evenly spaced grid. For example, as illustrated in FIG. 6A and FIG. 6B. Where, for example, step size between adjacent positions varies e.g., step size 650 is smaller than step size 652.

In some embodiments, e.g. as illustrated in FIG. 6C, possible positions from a starting position 656 are centered on a circle 658 with radius corresponding to the step size (exemplary possible positions from starting position 656 illustrated in FIG. 6C by dashed circles).

In some embodiments, upon failed pick-up in a first position, the probe is moved to a second position adjacent (e.g. one step size away) to the first position e.g. as illustrated by arrows in FIGS. 6A-6C.

In some embodiments, a step size is 0.1 mm-50 mm, or 0.5-20 mm, or 1-5 mm, or lower or higher or intermediate sizes or ranges.

In some embodiments, step size is selected based on a probe tip area. For example, in order for the step size to provide dense coverage of the container with a given probe tip, e.g. as illustrated in FIG. 6B where distance between possible locations is minimized. In some embodiments, a step size is 0.5, or 1, or 2, or 0.1-5, or 0.5-2 times, or lower or higher or intermediate multiples or ranges, of a cross sectional diameter of a probe tip or maximum cross sectional extent at the probe tip, in the case of non-circular probe tip cross section.

Alternatively or additionally, in some embodiments, step size is selected based on a dimension of a pill to be extracted with the probe. For example, the step size being 0.5, or 1, or 2, or 0.1-5, or 0.5-2 times a maximum dimension of the pill.

FIGS. 7A-7D are simplified schematics showing extraction of a pill 736 from a medication container 702, according to some embodiments of the invention.

In some embodiments, a probe 710 includes an opening 738, which, in some embodiments, e.g. as illustrated in FIGS. 7A-7D, is located at a tip of the probe.

Figure 7A:
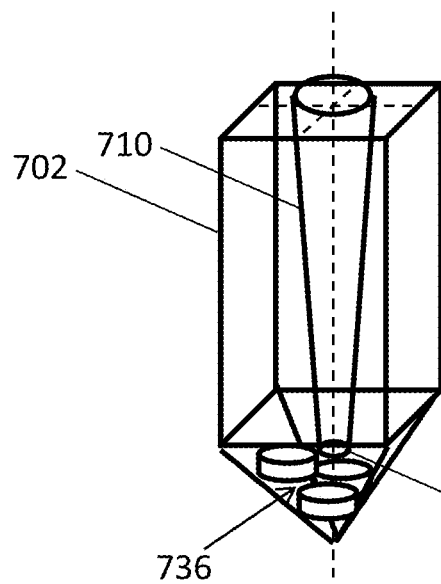
FIGS. 7A-7D are simplified schematics showing extraction of a pill from a medication container, according to some embodiments of the invention.

In FIG. 7A, a probe 710 has been inserted into medication container 702 but at the x-y position of insertion there is no pill sufficiently close to a tip 738 of the probe for suction at tip 738 to couple the pill to the probe tip.

Figure 7B:
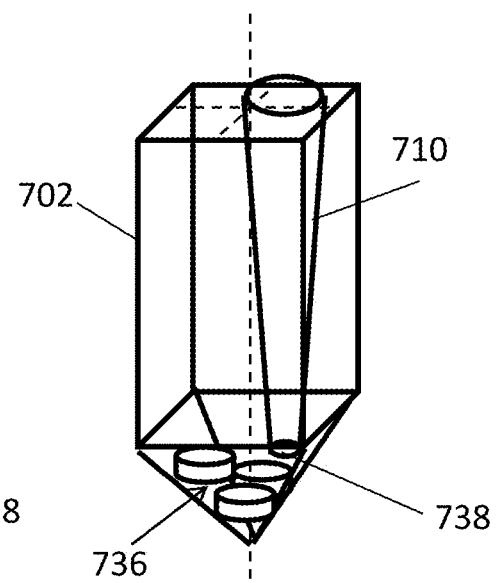

In FIG. 7B, the probe has been moved in the x-y plane, but there is still no pill sufficiently close to tip 738 of the probe for suction at tip 738 to couple the pill to the probe tip.

Figure 7C:
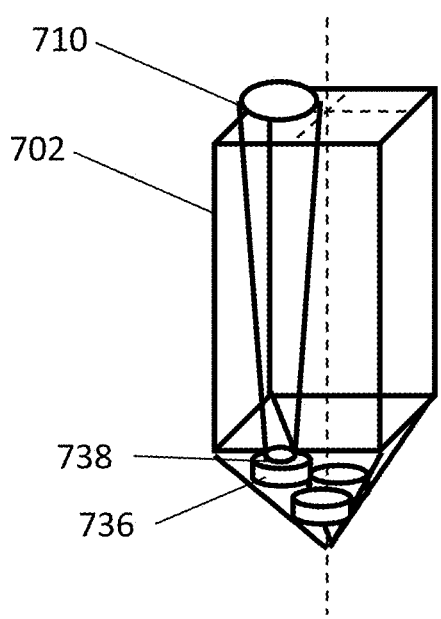

In FIG. 7C, the probe has been moved again in the x-y plane, to a new location and a pill is sufficiently close to tip 738 for suction at tip 738 to couple the pill to the probe tip.

Figure 7D:
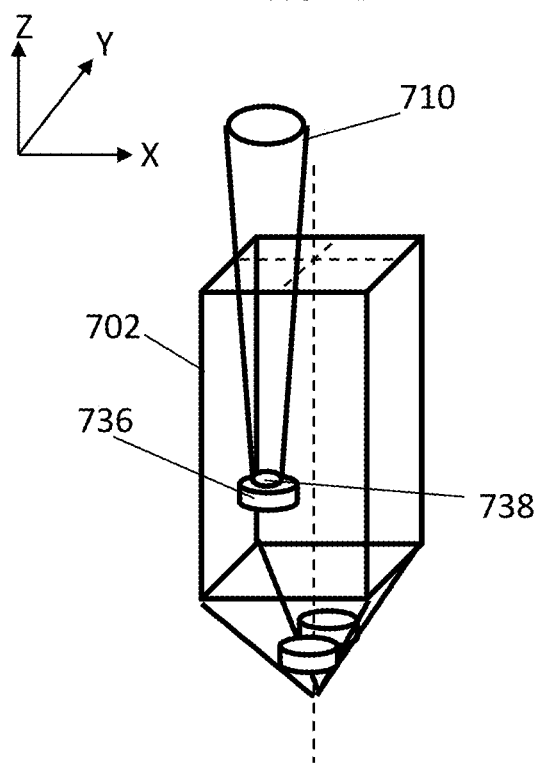

In FIG. 7D the probe is in the process of being lifted out of container 702, extracting pill 736.

FIGS. 8A-8E are simplified schematics showing extraction of a pill 836 from a medication container 802, according to some embodiments of the invention.

Figure 8A:
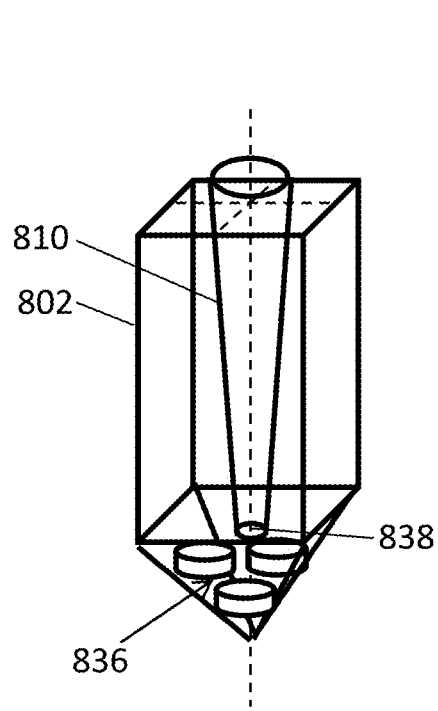
FIGS. 8A-8E are simplified schematics showing extraction of a pill from a medication container, according to some embodiments of the invention.

In FIG. 8A, a probe 810 has been inserted into medication container 802 but at the x-y position of insertion there is no pill sufficiently close to a tip 838 of the probe for suction at tip 838 to couple the pill to the probe tip.

Figure 8B:
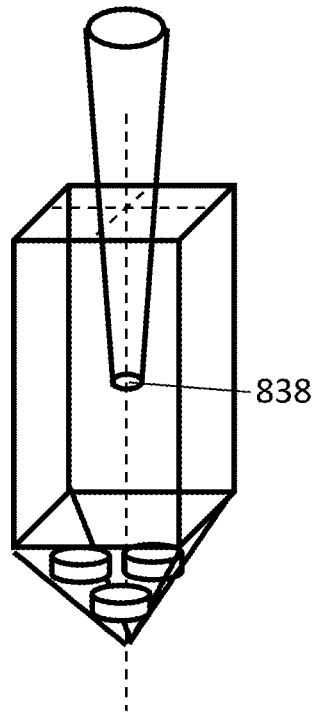
Figure 8C:
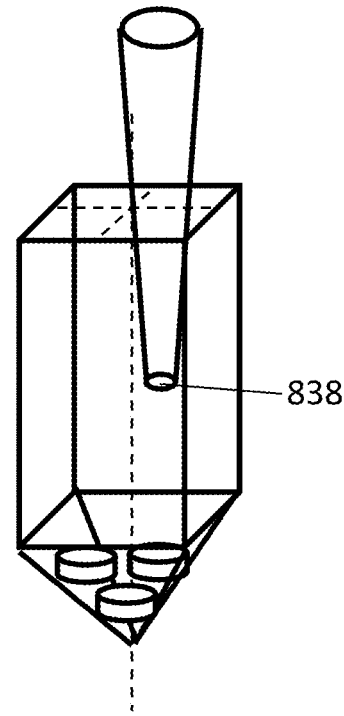

In FIG. 8B, probe 810 has been lifted (e.g. in the z direction) away from the pills before, in FIG. 8C probe is moved in the x-y plane.

Figure 8D:
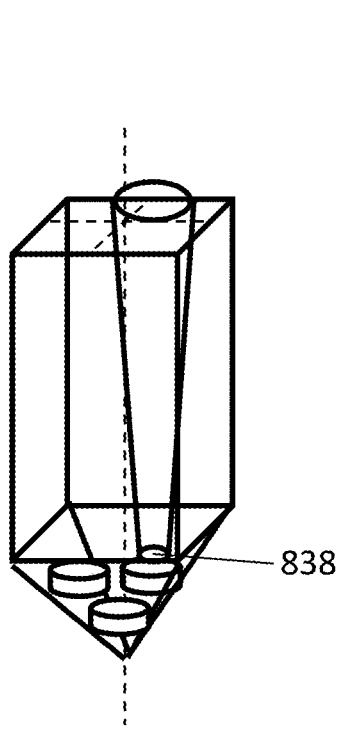
Figure 8E:
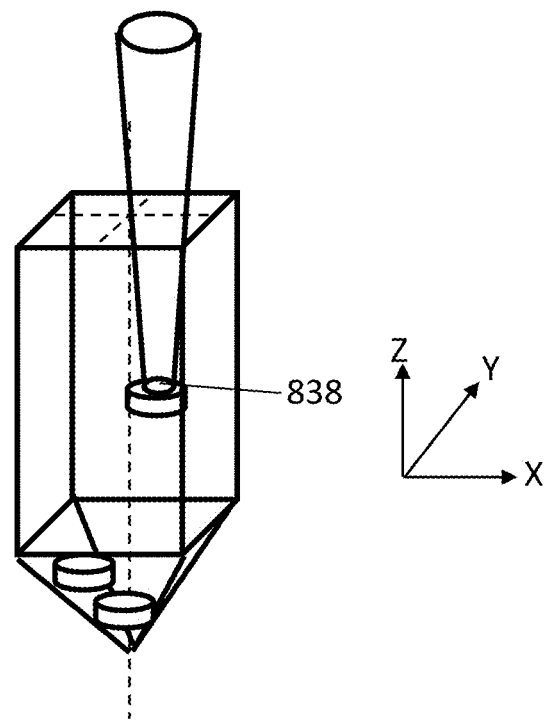

Once moved in the x-y plane, in FIG. 8C, the probe is re-inserted, sufficiently close to a pill 836 to couple the pill to the probe and, in FIG. 8D the probe is in the process of being lifted out of container 802, extracting pill 836.

Exemplary Apparatus

Figure 9A:
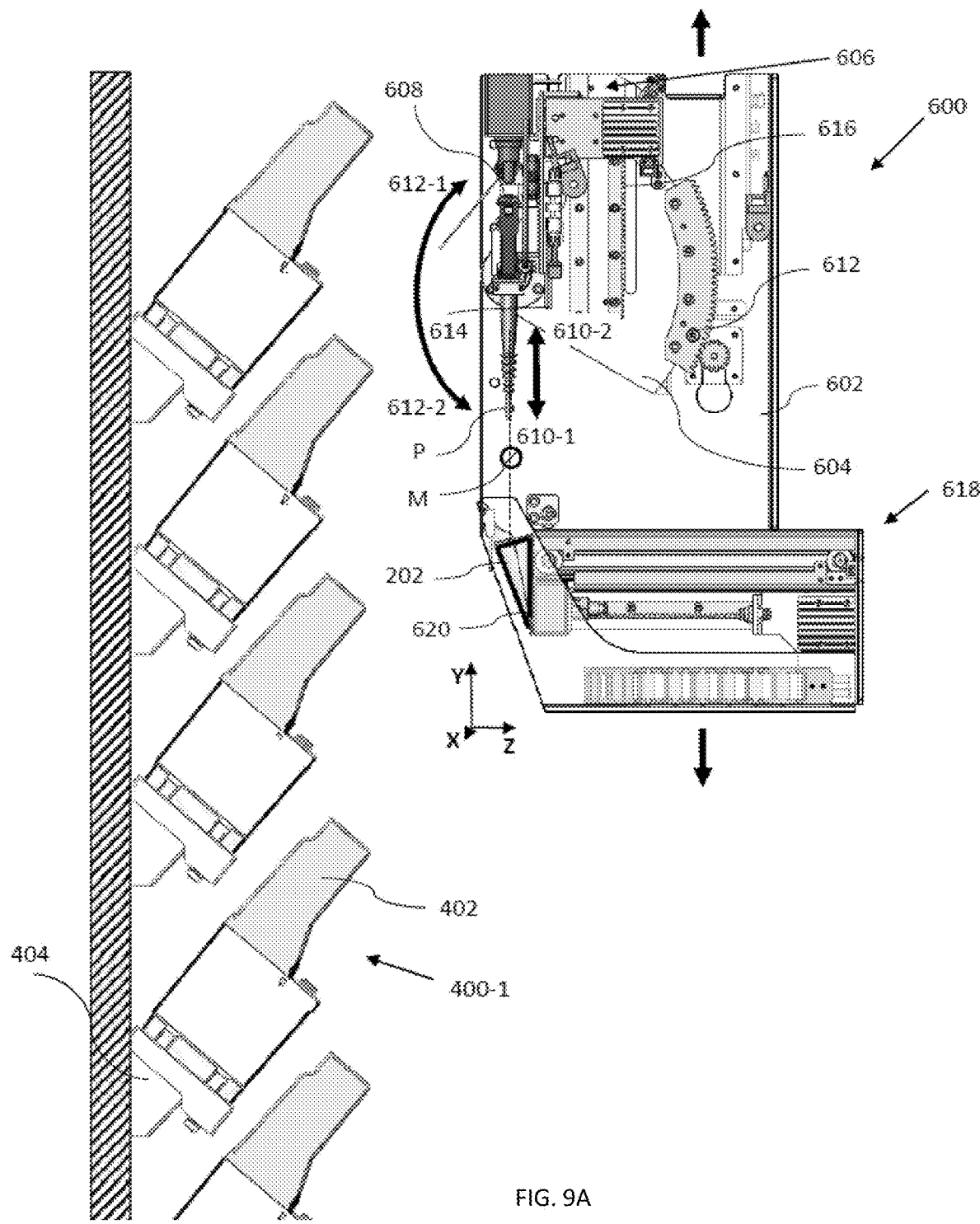
FIGS. 9A-9C, are simplified illustrations of a side view of a dispensing head, according to some embodiments of the invention.
Figure 9B:
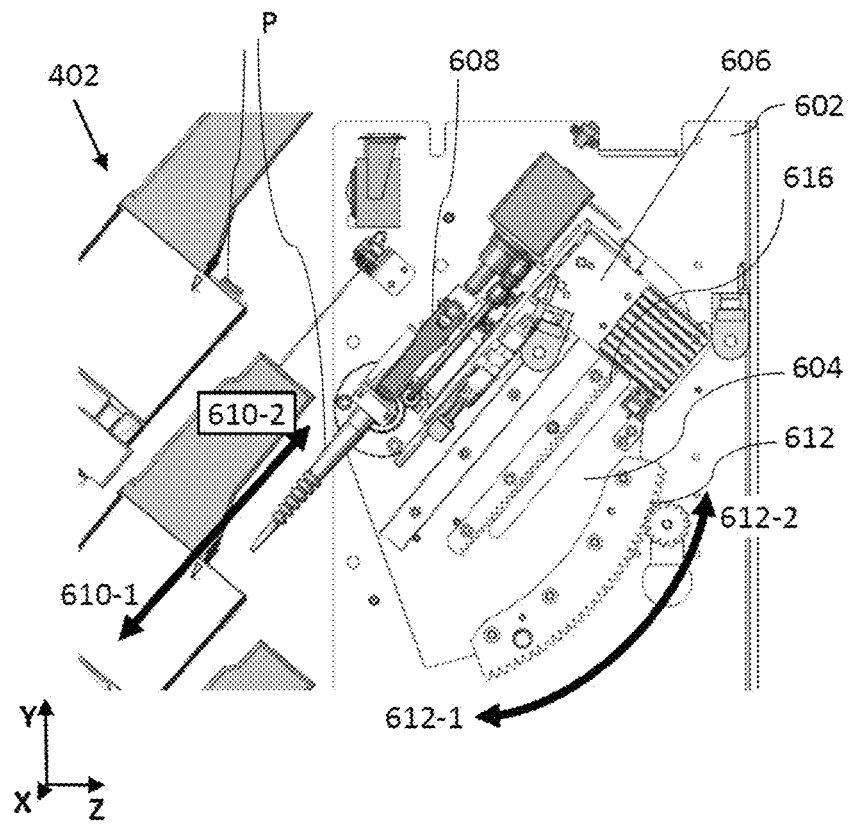
Figure 9C:
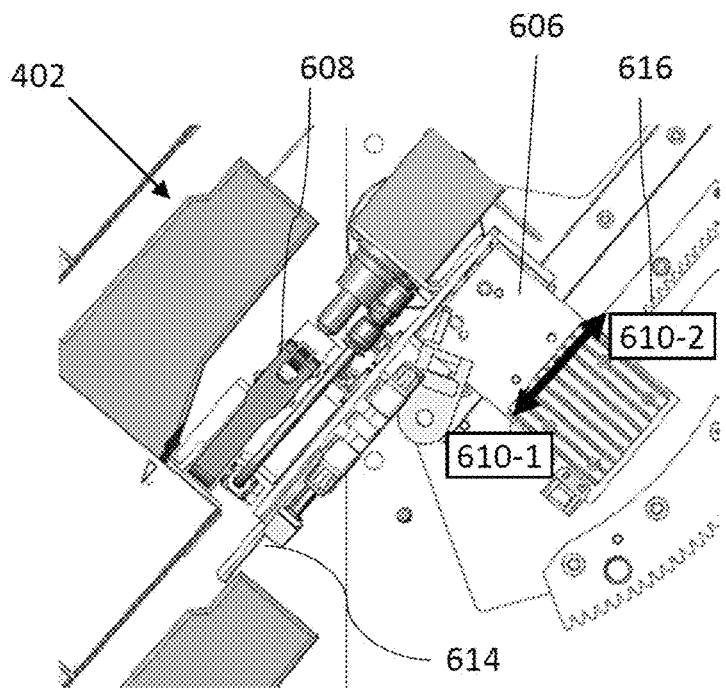

FIGS. 9A-9C, are simplified illustrations of a side view of a dispensing head, according to some embodiments of the invention.

As shown in FIG. 9A, dispensing head 600 is configured to move across a vertical panel 400-1 and approximate containers 402 coupled to panel 400-1. Head 600 is configured to move between containers 402 by a linear movement in a vertical direction Y. In some embodiments, the linear movement is a combination of horizontal movements in direction X and vertical movement in direction Y across panel 400-1.

As shown in FIGS. 9A and 9B, dispensing head 600 includes a head housing 602. In some embodiments, head 600 has a movable platform 604, rotatably coupled to housing 602.

According to some embodiments, head 600 includes a gripper module 606, coupled to platform 604, and a gripper 608 coupled to gripper module 606 and configured for picking a probe P coupled to a medication container 402.

As shown in FIGS. 9A to 9C, in some embodiments, gripper module 606 is linearly moveable in respect to housing 602 in a proximal direction 610-1 and a distal direction 610-2. In some embodiments, gripper module 606 is configured to actuate gripper 608 for grabbing a probe P from the container by approximating gripper 608 to the probe P in a proximal direction 610-1, and grabbing the probe away of the container by a distal linear motion in direction 610-2. In some embodiments, returning of probe P to the container is by actuating gripper 608 by gripper module 606 in a proximal linear motion towards of the container in direction 610-1. In some embodiments, moving gripper 608 in proximal direction 610-1 and distal direction 610-2 is without moving housing 602 in respect to the medications panel (such as 400-1). In some embodiments, proximal direction 610-1 and distal direction 610-2 are vertical in direction Y.

According to some embodiments, rotating gripper 608 in respect to the medications panel is without rotating housing 602 and without moving head 600. In some embodiments, for example as shown in FIGS. 9A and 9B, head 600 includes a gear mechanism 612, interconnecting platform 604 and housing 602. In some embodiments, rotating of platform 604 by gear 612, rotates gripper 608 in directions 612-1 (shown in FIG. 9B) and 612-2 (shown in FIG. 9A). In some embodiments, rotational directions 612-1 and 612-2 are about axis X which is perpendicular to axes Y and Z.

In some embodiments, head 600 includes a linear gear mechanism 616, interconnecting gear module 606 and housing 602. In some embodiments, moving of gear module 606 by gear 616, moves gripper 608 in directions 610-1 (shown in FIG. 9C) and 610-2 (shown in FIGS. 9A and 9B). In some embodiments, linear gear mechanism 616 interconnects gear module 606 and platform 604. In some embodiments, connecting gear 616 to platforms 604, enables actuating of gripper 608 and/or reader 614 in both linear and rotation motion in respect to housing 602.

According to some embodiments, dispensing head 600 includes envelope carrier 618 for coupling one or more medication envelopes (such as 202) to head 600. In some embodiments, for example as shown in FIG. 9A, envelope carrier 618 is coupled to housing 602, below gripper 608. According to some embodiments, envelope carrier 618 includes envelope mount 620, which is configured to hold an envelope (e.g. 202) when dispensing medication dosage into the envelope. As shown in FIG. 9A, envelope mount 620, is holding envelope 202 vertically under gripper 608. In some embodiments, when a probe P is used to hold the medication dosage, envelope mount 620, is holding envelope 202 vertically under the tip of the probe P, such as a medication disposed at the tip of the probe is dispensed by dropping the medication M from the probe P into the open envelope.

In some embodiment, holding the envelope is by suction power applied to a surface of the envelope by mount 620. In some embodiments, a suction system (such as 520) is connected to envelope carrier 618 to provide suction to a suction port disposed in mount 620.

Exemplary Probes and Exemplary Probe Selection

In some embodiments, the probe is configured to minimize potential damage associated movement of the probe within the container, including impacts between the container and/or pills within the container and the probe.

In some embodiments, the probe e.g. probe tip includes soft material, for example material softer than that of the pills to be extracted e.g. rubber e.g. sponge. For example, in some embodiments, the probe includes a soft and/or compressible coating and/or tip.

In some embodiments, the probe includes a collapsible and/or elastically deformable structure. For example, in some embodiments, the probe includes a concertina structure, which is configured to contract in a direction of a long axis of the probe and/or in a direction of insertion of the probe. In some embodiments, the concertina structure is flexible (e.g. elastically deflectable) in directions perpendicular to the long axis of the probe and/or direction of insertion of the probe.

In some embodiments, the probe comprises (e.g. is made from) rubber e.g. silicone rubber. Alternatively or additionally, in some embodiments, the probe comprises plastic and/or metal.

In some embodiments, the probe is tubular structure, which, in some embodiments, is elastic. For example, elastically deflectable e.g. at least in one or more direction perpendicular to a long axis of the probe.

In some embodiments, the probe is a metal tubular structure. In some embodiments, the probe is a plastic tubular structure.

In some embodiments, the probe includes a disposable and/or replaceable portion e.g. tip. Where, for example, in some embodiments, the probe tip is replaced after a time duration and/or after each use, for example, after dispensing of a particular medication and/or of a patient's medication, potentially reducing contamination. In some embodiments, a tip of the probe is extended (e.g. to an original length) after removal of the tip (e.g. a probe sheath is unrolled to extend the probe).

FIGS. 10A-10B are simplified schematic top views of a container 1002 containing pills 1036 with a cross section of a probe at the probe tip 1038 superimposed on the top view, according to some embodiments of the invention.

FIGS. 10A-10B illustrate use, in some embodiments, of larger tip size for extraction of larger pills (FIG. 10B compared to FIG. 10A). Potentially a larger tip size enables coupling with lower pressure, potentially reducing and/or preventing damage to the pill. Additionally or alternatively, a larger tip is advantageous for larger pills as space between the pills may be correlated with the pill size and the larger tip, potentially, is more likely to overlap a pill at any given position.

In some embodiments, a probe tip internal cross sectional area selected to be 10-90%, or 10-80%, or 10-50%, or lower or higher or intermediate percentages or ranges, of an average pill dimension, or of a minimum pill dimension, or of a maximum pill dimension (e.g. one or more of maximum, minimum, average pill dimensions as defined in the text regarding step 416, FIG. 4B).

FIGS. 11A-11D are simplified schematics of a probe 1110 coupled to pills, according to some embodiments of the invention.

FIGS. 12A-12B are simplified schematics of a probe coupled to pills, according to some embodiments of the invention.

In some embodiments, a pill couples (e.g. sufficiently couples for the probe to extract the pill) to a probe opening when a minimum percentage of the probe opening is covered by the pill and/or when a minimum percentage of a perimeter of the opening is in contact with the pill surface. Where, in some embodiments, the minimum percentages are 10-95%, or 20-80%, or lower or higher or intermediate ranges or percentages.

In some embodiments, a strength of coupling of a pill to a probe tip depends on an orientation of a pill with respect to the probe tip e.g. as illustrated in FIGS. 11A-C and FIGS. 12A-12B.

In some embodiments, a probe opening (e.g. probe tip) is configured to provide a high level of contact between the suction provided at the opening and the pills to be extracted. For example, without sucking the pill into the probe e.g. beyond a maximum depth within the probe.

Figures 13A, 13B:
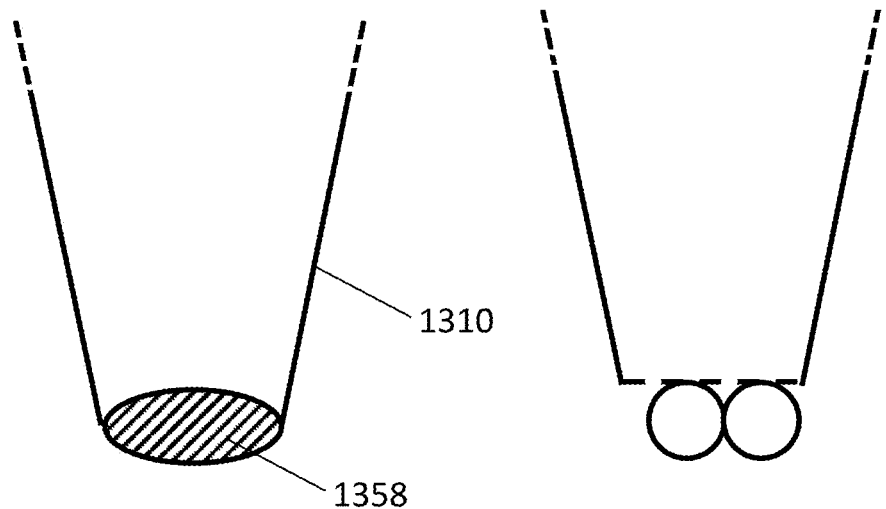
FIG. 13A is a simplified schematic of a probe with a mesh covered tip, according to some embodiments of the invention.
FIGS. 13B-13D are simplified schematic cross sections of a probe with a mesh covered tip, coupled to pills, according to some embodiments of the invention.

FIG. 13A is a simplified schematic of a probe 1310 with a mesh covered tip 1258, according to some embodiments of the invention.

A potential advantage of a probe with a mesh covered tip is the ability to couple a range of size of pills to the probe without the pills being sucked into the probe.

A further potential advantage is the ability to extract more than one pill using the probe, at the same time. In some embodiments, a mesh covered tip is used in conjunction with a weight sensor, for dispensing of a desired number of pills. In some embodiments, an imager is used to provide feedback as to whether a desired number of pills has been coupled to the probe.

Figures 13C, 13D:
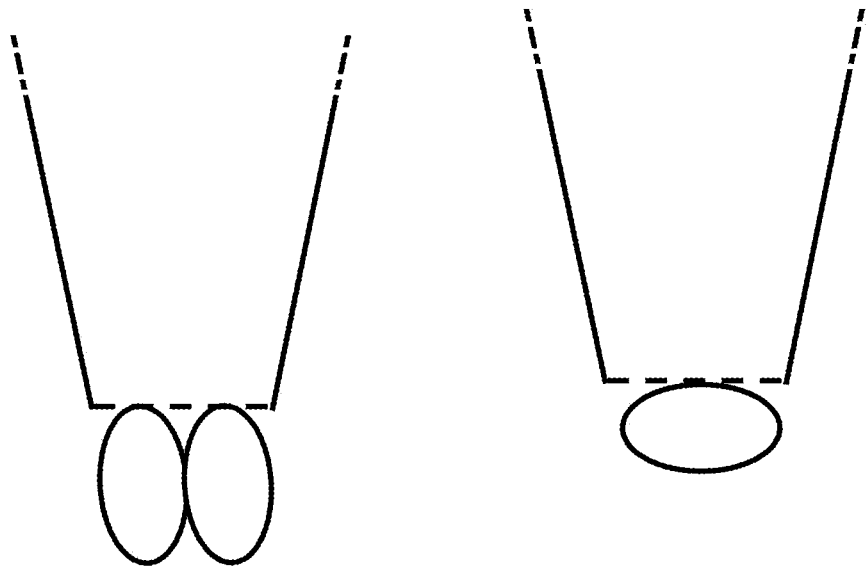

FIGS. 13B-13D are simplified schematic cross sections of a probe with a mesh covered tip, coupled to pills, according to some embodiments of the invention.

In some embodiments, one or more of FIGS. 13B-D show a cross section of the probe of FIG. 13A.

In some embodiments, a probe is configured to couple to a range of dimensioned pills. For example, in some embodiments, a probe opening includes a tapered inlet, pills entering into the probe opening, at a depth associated with dimensions of the pills.

Figure 14:
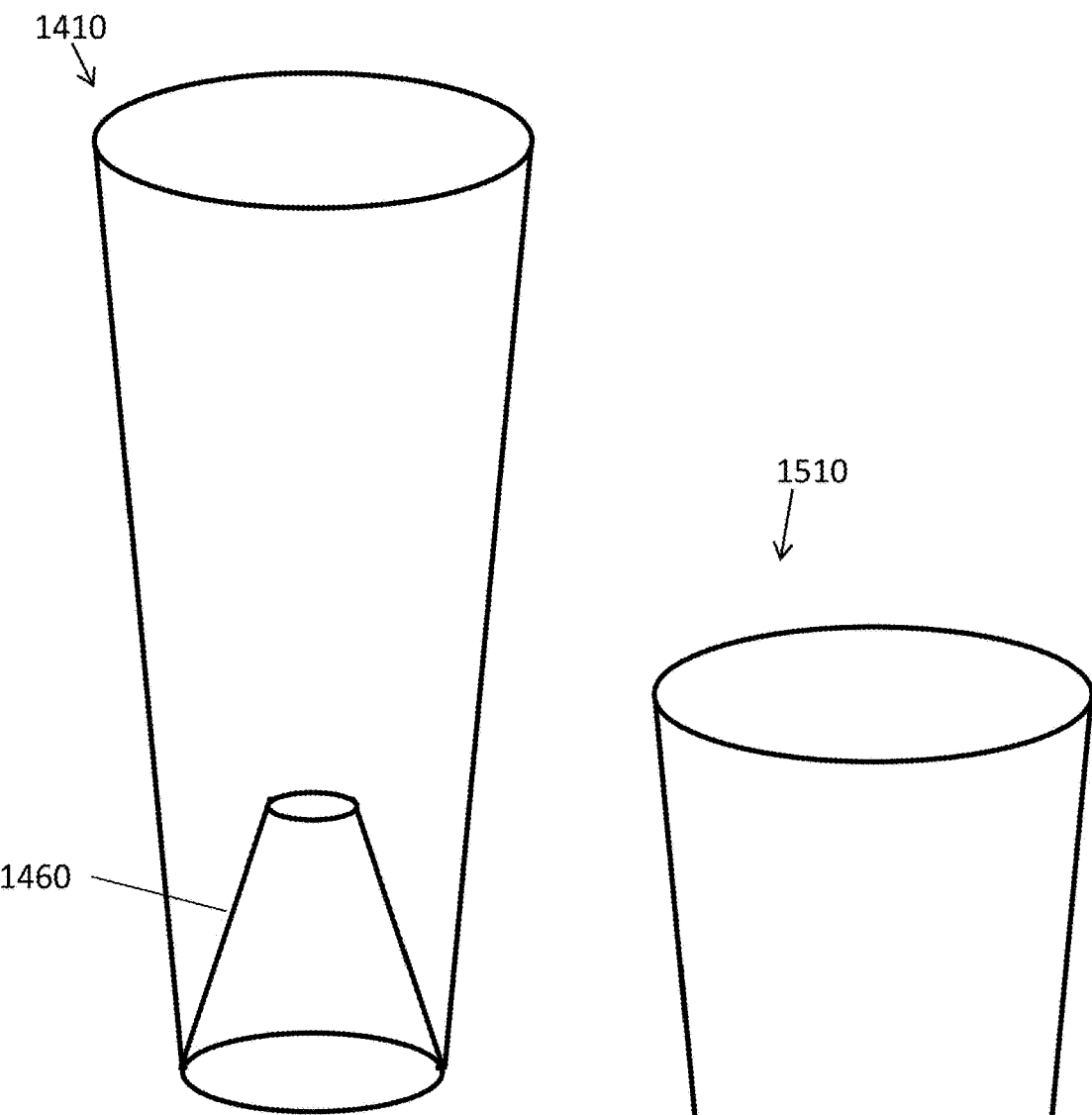
FIG. 14 is a simplified schematic of a probe with a tapering inlet, according to some embodiments of the invention.

FIG. 14 is a simplified schematic of a probe 1410 with a tapering inlet 1460, according to some embodiments of the invention.

In some embodiments, a probe inlet includes flexible material, in some embodiments, flexibly at least partially matching a shape of the inlet to the pill to be collected. Potentially improving coupling of the probe to the pill to be extracted.

Figure 15:
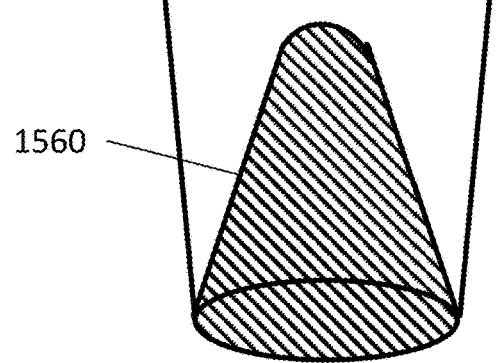
FIG. 15 is a simplified schematic of a probe with probe tip enclosed by a low tension mesh, according to some embodiments of the invention.

FIG. 15 is a simplified schematic of a probe with probe tip enclosed by a low tension mesh, according to some embodiments of the invention.

In some embodiments, a probe is selected to match geometry of a pill to be collected, for example, a cross section of an opening of a probe is selected based on the pill shape. For example, in some embodiments, ovalic shape pills are collected using a probe tip with ovalic cross section, in some embodiments, spherical pills are collected using a probe tip with circular cross section.

Figures 16A, 16B:
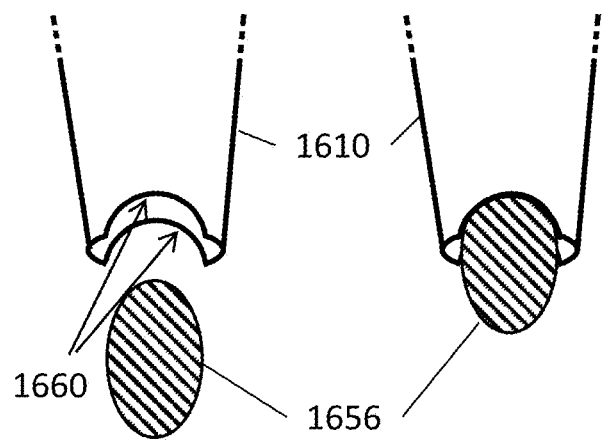
FIGS. 16A-16B are simplified schematics of coupling of a pill to a probe with curved inlets at the probe tip, according to some embodiments of the invention.

FIGS. 16A-16B are simplified schematics of coupling of a pill 1656 to a probe 1610 with curved inlets 1660 at the probe tip, according to some embodiments of the invention. A potential advantage of a curved tip is better sealing between the pill 1556 and the probe tip, for example, when the curvature of the probe matches that of the pill.

In some embodiments, a single probe includes more than one suction channel. For example, for extraction of more than one pill at the same time. For example, a single pill per suction channel.

Figure 17:
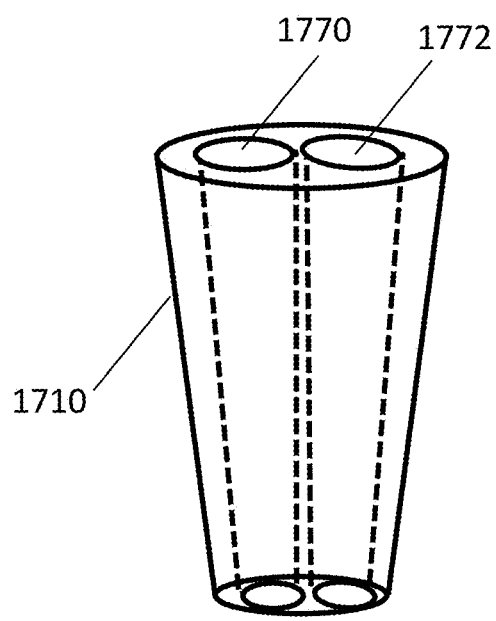
FIG. 17 is a simplified schematic of a multi-channel probe, according to some embodiments of the invention.

FIG. 17 is a simplified schematic of a multi-channel probe 1710, according to some embodiments of the invention. In some embodiments, probe 1710 includes two or more suction channels 1770, 1772, for example, 2-10, or 2-5, or lower or higher or intermediate numbers of suction channel.

In some embodiments, more than one probe is inserted into the container, for example, to extract more than one pill e.g. one or more pill per probe.

General

It is expected that during the life of a patent maturing from this application many relevant medication types, medication containers, and medication dispensers will be developed and the scope of the terms medication types, medication containers, and medication dispensers is intended to include all such new technologies a priori.

As used herein the term "about" refers to ±20%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first, indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of dispensing medication from a plurality of medication containers, using a dispensing system for collecting a medication dosage from a medication container and moving it into a medication receptacle for dispensing, the method comprising:
receiving a medication selection;
selecting a medication container, from said plurality of medication containers, based on said medication selection;
matching a collection protocol to be applied to said medication container including one or more parameter for control of said dispensing system; and
dispensing said medication selection from said medication container according to said collection protocol;
wherein said method further comprises receiving a weight measurement signal from at least one weight sensor; and
determining successful delivery of said medication selection into said medication receptacle based on said weight measurement signal.

2. The method according to claim 1, wherein said at least one weight sensor is located at said medication receptacle.

3. The method according to claim 1, wherein said at least one weight sensor is located at said medication container.

4. The method according to claim 1, wherein said dispensing system comprises a probe, said method comprising:
inserting said probe into said selected medication container; and
collecting said medication selection with said probe.

5. The method according to claim 4, wherein said at least one weight sensor is located at said probe.

6. The method according to claim 4, wherein said collecting comprises applying suction, according to said collection protocol.

7. The method according to claim 6, wherein said inserting comprises inserting said probe to an initial depth at an initial position, said initial depth and said initial position according to said collection protocol.

8. The method according to claim 6, wherein said collection protocol includes one more of:
one or more parameter based on medication data associated with said medication selection; and
one or more parameter based on medication container data.

9. The method according to claim 8, wherein said medication data comprises a weight of a pill of said medication selection;
wherein said collection protocol comprises a suction parameter based on said weight.

10. The method according to claim 8, wherein said medication data comprises a least one dimension of a pill of medication selection; and
wherein said collection protocol comprises a movement parameter based on at least one dimension.

11. The method according to claim 8, wherein said medication container data comprises at least one position within the container, of a previously successful pill extraction;
wherein said initial position is based on said at least one position.

12. The method according to claim 8, comprising receiving a measurement signal; and
determining a quality of coupling of a pill to said probe, based on said measurement signal;
changing at least one parameter of said collection protocol if said determining indicates that quality of coupling is insufficient.

13. The method according to claim 12, wherein said at least one parameter comprises a position of said probe in said medication container.

14. The method according to claim 13, comprising:
measuring a proximity measurement signal of proximity of an opening of said probe to a pill; and
wherein said changing comprises moving said probe to a position based on said proximity measurement signal.

15. The method according to claim 14, wherein said proximity measurement signal is a visual measurement signal.

16. The method according to claim 13, wherein said inserting comprises inserting said a probe in a first direction into said medication container to an initial depth at an initial position on a plane perpendicular to said first direction;
wherein said position is a position of said probe on said plane, said changing thereby changing a position of said probe.

17. The method according to claim 16, wherein said position is a step size in distance from said initial position, said step size depending on medication data and/or container data.

18. The method according to claim 15, wherein said medication data includes at least one pill dimension;
wherein said container data includes one or more historical successful extraction position.

19. The method according to claim 12, comprising repeating said determining and said changing until said determining indicates that said quality is sufficient.

20. The method according to claim 19, comprising removing said probe and said pill from said medication container.

21. The method according to claim 19, comprising saving a position of said probe when said quality is sufficient.

22. The method according to claim 12, wherein said changing comprises changing a suction level, based on medication data.

23. The method according to claim 22, wherein said medication data includes one or more of:
a pill weight;
historical successful suction levels.

24. The method according to claim 12, wherein said determining comprises one or more of:
receiving a probe suction level measurement;
receiving a weight measurement of said medication container; and
receiving a weight measurement of said probe.

25. The method according to claim 16, wherein said initial depth is based on a fullness level of said medication container.

26. The method according to claim 25, wherein said fullness is determined using one or more of:
a value received from a memory; and
a measurement signal comprising one or more of:
a weight measurement; and
a proximity detection measurement.

27. The method according to claim 16, wherein said inserting comprises selecting a probe based on said pill property data.

28. The method according to claim 12, wherein said determining comprises:
reducing suction for a time period; and
comparing said measurement signal before said time period and after said time period.

29. The method according to claim 4, wherein said medication selection comprises a desired number of pills, said method comprising:
  receiving a measurement signal;
  determining a number of pills coupled to said probe, based on said measurement signal;
  changing at least one parameter of said collection protocol if said determining indicates that the number of pills coupled is less or more than said desired number of pills.

30. The method according to claim 29, wherein said determining comprises:
  reducing suction for a time period; and
  comparing said measurement signal before said time period and after said time period.

31. A dispensing system for collecting a medication dosage from a medication container and moving it into a medication receptacle for dispensing, the system comprising:
  a suction source;
  a probe connected to said suction source and configured to apply suction from said suction source at a probe opening;
  one or more actuator configured to move said probe to said medication container and into sufficient proximity to said medication dose to couple said medication dose to said probe under said suction at said probe opening;
  a receptacle carrier comprising at least one medication receptacle; said receptacle carrier comprising at least one weight sensor configured for measuring a weight of said at least one medication receptacle for determining a successful delivery of said medication dosage into said medication receptacle based on a weight measurement signal.

32. The dispensing system according to claim 31, wherein said at least one weight sensor is located at said medication receptacle.

33. The dispensing system according to claim 31, wherein said at least one weight sensor is located at said medication container.

34. The dispensing system according to claim 31, wherein said determining comprises measuring a weight of said at least one medication receptacle for determining that a correct medication dosage was delivered to said medication receptacle according to a weight of said medication dosage.

35. The dispensing system of claim 34, wherein said one or more actuator is configured to move said probe into said medication container.

36. The dispensing system of claim 35, wherein said one or more actuator is configured to move said probe within said medication container.

* * * * *